US011369749B2

(12) United States Patent
Koehler et al.

(10) Patent No.: US 11,369,749 B2
(45) Date of Patent: *Jun. 28, 2022

(54) TIP PROTECTOR FOR A SAFETY CATHETER

(71) Applicant: Smiths Medical ASD, Inc., Plymouth, MN (US)

(72) Inventors: Thomas T Koehler, Simsbury, CT (US); Kathryn L Felicito, Cheshire, CT (US); Harsh Chheda, Cheshire, CT (US); Oscar R Abriles, Madison, CT (US)

(73) Assignee: SMITHS MEDICAL ASD, INC., Plymouth, MN (US)

( * ) Notice: Subject to any disclaimer, the term of this patent is extended or adjusted under 35 U.S.C. 154(b) by 353 days.

This patent is subject to a terminal disclaimer.

(21) Appl. No.: 16/396,515

(22) Filed: Apr. 26, 2019

(65) Prior Publication Data

US 2019/0262549 A1 Aug. 29, 2019

Related U.S. Application Data

(60) Continuation of application No. 15/383,217, filed on Dec. 19, 2016, now Pat. No. 10,314,984, which is a
(Continued)

(51) Int. Cl.
*A61M 5/32* (2006.01)
*A61M 5/162* (2006.01)
*A61M 25/06* (2006.01)

(52) U.S. Cl.
CPC ........ *A61M 5/3213* (2013.01); *A61M 5/1626* (2013.01); *A61M 5/321* (2013.01);
(Continued)

(58) Field of Classification Search
CPC .. A61M 5/3213; A61M 5/1626; A61M 5/321; A61M 5/329; A61M 25/0618; A61M 25/0637
See application file for complete search history.

(56) References Cited

U.S. PATENT DOCUMENTS

| 4,944,725 A | 7/1990 | McDonald |
| 4,952,207 A | 7/1990 | Lemieux |

(Continued)

FOREIGN PATENT DOCUMENTS

| CN | 1547493 | 11/2004 |
| CN | 101500637 | 8/2009 |

(Continued)

OTHER PUBLICATIONS

Extended European Search Report dated Apr. 14, 2014 in European Application No. 14161101.2.
(Continued)

*Primary Examiner* — Theodore J Stigell
(74) *Attorney, Agent, or Firm* — Louis Woo

(57) ABSTRACT

A safety catheter includes a catheter hub, a needle cannula having a tip, and a tip protector. The tip protector includes an outer member and an inner member therein. The outer member has a projection releasably engaging the catheter hub. The inner member has a pair of arms extending to free ends from a base. The inner member is axially shiftable relative to the outer member between a first position wherein the needle tip is distal of the tip protector and the free ends of the arms are spread apart such that the distal tip is not shielded, and a second position wherein the tip is within the inner and outer members and the free ends of the arms are brought into close proximity such that the distal tip is
(Continued)

shielded. The inner member is entirely received within the outer member in both the fort and the second positions thereof.

12 Claims, 21 Drawing Sheets

Related U.S. Application Data continuation of application No. 13/564,396, filed on Aug. 1, 2012, now Pat. No. 9,555,220, which is a division of application No. 12/792,290, filed on Jun. 2, 2010, now Pat. No. 8,257,322.

(52) U.S. Cl.
CPC ........ *A61M 5/329* (2013.01); *A61M 25/0618* (2013.01); *A61M 25/0637* (2013.01)

(56) References Cited

U.S. PATENT DOCUMENTS

| | | | |
|---|---|---|---|
| 4,964,854 A | 10/1990 | Luther | |
| 5,458,658 A | 10/1995 | Sircom | |
| 5,599,310 A | 2/1997 | Bogert | |
| 5,676,656 A | 10/1997 | Brimhall | |
| 6,117,108 A | 9/2000 | Woehr et al. | |
| 6,221,047 B1 | 4/2001 | Greene et al. | |
| 6,287,278 B1 | 9/2001 | Woehr et al. | |
| 6,379,333 B1 | 4/2002 | Brimhall et al. | |
| 6,595,954 B1 | 7/2003 | Luther et al. | |
| 6,616,630 B1 | 9/2003 | Woehe et al. | |
| 6,689,102 B2 | 2/2004 | Greene | |
| 6,709,419 B2 | 3/2004 | Woehr | |
| 6,749,588 B1 | 6/2004 | Howell et al. | |
| 7,125,397 B2 | 10/2006 | Woehr et al. | |
| 7,214,211 B2 | 5/2007 | Woehr et al. | |
| 7,658,725 B2 | 2/2010 | Bialecki et al. | |
| 7,785,296 B2 | 8/2010 | Muskatelo et al. | |
| 7,828,774 B2 | 11/2010 | Harding et al. | |
| 8,257,322 B2 * | 9/2012 | Koehler | A61M 5/1626 604/263 |
| 9,555,220 B2 * | 1/2017 | Koehler | A61M 25/0637 |
| 10,314,984 B2 * | 6/2019 | Koehler | A61M 5/321 |
| 2003/0060771 A1 | 3/2003 | Bialecki et al. | |
| 2004/0204681 A1 | 10/2004 | Thoresen et al. | |
| 2004/0225260 A1 | 11/2004 | Villa et al. | |
| 2004/0236288 A1 | 11/2004 | Howell et al. | |
| 2005/0027263 A1 | 2/2005 | Woehr et al. | |
| 2005/0080378 A1 | 4/2005 | Cindrich et al. | |
| 2005/0096592 A1 | 5/2005 | Carlyon | |
| 2005/0113755 A1 | 5/2005 | Greene et al. | |
| 2005/0182363 A1 | 8/2005 | Kuli | |
| 2007/0093778 A1 | 4/2007 | Cindrich et al. | |
| 2007/0112305 A1 | 5/2007 | Brimhall | |
| 2008/0249478 A1 | 10/2008 | Ishikura et al. | |
| 2009/0182280 A1 | 7/2009 | Glowaki et al. | |
| 2009/0281499 A1 * | 11/2009 | Harding | A61M 25/0618 604/164.08 |
| 2010/0015804 A1 | 1/2010 | Muskatello et al. | |
| 2010/0168675 A1 | 7/2010 | Cindrich et al. | |
| 2010/0222746 A1 * | 9/2010 | Burkholz | A61M 25/0618 604/164.08 |
| 2010/0222749 A1 | 9/2010 | Baid | |
| 2010/0241087 A1 * | 9/2010 | Moulton | A61M 25/0618 604/263 |
| 2011/0213307 A1 | 9/2011 | Kawai et al. | |
| 2011/0301551 A1 | 12/2011 | Koehler et al. | |

FOREIGN PATENT DOCUMENTS

| | | |
|---|---|---|
| CN | 101543657 | 9/2009 |
| EP | 1974765 | 10/2008 |
| EP | 2343095 | 7/2011 |
| EP | 2575946 | 4/2013 |
| EP | 2745870 | 6/2014 |
| JP | 2004-073403 | 3/2004 |
| JP | 6808798 | 6/2013 |
| WO | 9008564 | 8/1990 |
| WO | 0123028 | 4/2001 |
| WO | 0123029 | 4/2001 |
| WO | 0193940 | 12/2001 |
| WO | 03011381 | 2/2003 |
| WO | 2004/000408 | 12/2003 |
| WO | 2006062963 | 6/2006 |
| WO | 2008/021132 | 2/2008 |
| WO | 2009/010847 | 1/2009 |
| WO | 2009139951 | 11/2009 |
| WO | 2009154824 | 12/2009 |
| WO | 2010008784 | 1/2010 |
| WO | 2010/038471 | 4/2010 |
| WO | 2010101740 | 9/2010 |
| WO | 2011/036574 | 11/2010 |
| WO | 2011/036574 | 3/2011 |
| WO | 2011152916 | 12/2011 |

OTHER PUBLICATIONS

Office Action dated Aug. 1, 2014 in Japanese Application No. 2013-513163.
Internatioal Preliminary Report on Patentability dated Aug. 21, 2012 in Application No. PCT/US2011/028770.
International Search Report dated May 19, 2011 in Application No. PCT/US2011/028770.
Examination Report No. 1 dated May 5, 2015 in Australian Application No. 2011261837.
Office Action dated Apr. 3, 2015 in Chinese Application No. 201180020786.8.
Office Action dated Sep. 4, 2014 in Chinese Application No. 201180020786.8.
Notice of Acceptance dated Apr. 28, 2016 in Australian Application No. 2011261837.
Office Action dated Sep. 18, 2013 in U.S. Appl. No. 13/564,396.
Office Action dated Jun. 5, 2014 in U.S. Appl. No. 13/564,396.
Final Office Action dated Nov. 21, 2014 in U.S. Appl. No. 13/564,396.
Office Action dated Feb. 12, 2016 in U.S. Appl. No. 13/564,396.
Notice of Allowance dated Jun. 6, 2016 in U.S. Appl. No. 13/564,396.
Notice of Allowance dated Sep. 21, 2016 in U.S. Appl. No. 13/564,396.
Communication Under Rule 71(3) EPC dated Jun. 2, 2016 in European Application No. 14161101.2.
Office Action dated Aug. 17, 2017 in Canadian Application No. 2,791,402.
Office Action dated Jun. 4, 2018 in U.S. Appl. No. 15/383,217.
Final Ofice Action dated Dec. 3, 2019 in U.S. Appl. No. 15/383,217.

* cited by examiner

TIP PROTECTOR FOR A SAFETY CATHETER

CROSS-REFERENCE TO RELATED APPLICATIONS

This application is a continuation of, claims priority to and the benefit of, U.S. Ser. No. 15/383,217 filed Dec. 19, 2016 and entitled "TIP PROTECTOR FOR A SAFETY CATHETER." The '217 application is a continuation of, claims priority to and the benefit of, U.S. Ser. No. 13/564, 396 filed Aug. 1, 2012 and entitled "TIP PROTECTOR FOR A SAFETY CATHETER," which issued as U.S. Pat. No. 9,555,220 on Jan. 31, 2017. The '396 application is a divisional of, claims priority to and the benefit of, U.S. Ser. No. 12/792,290 filed Jun. 2, 2010 and entitled "TIP PROTECTOR FOR A SAFETY CATHETER," which issued as U.S. Pat. No. 8,257,322 on Sep. 4, 2012. All three of the aforementioned applications are incorporated herein by reference in their entirety.

FIELD OF INVENTION

The present invention relates to safety catheters and, more particularly, to tip protectors to shield the sharp tip of the needle cannula used with the catheter.

BACKGROUND OF INVENTION

Safety catheters are widely used and typically include a catheter hub with a catheter tube extending distally thereof to be placed intravenously, a needle hub or support with a needle cannula extending distally thereof to a sharp distal tip and extending through the catheter tube to expose the sharp tip in order to facilitate intravenous insertion of the catheter tube, and a tip protector through which at least a portion of the needle shaft passes and adapted to enclose or otherwise shield the tip of the needle cannula after it has been withdrawn from the catheter tube and into the tip protector.

One form of tip protector involves a clip that fits within the catheter hub. Such clips are readily recognized in that they are thin webs of metal or the like which are bent or otherwise formed to have a back wall and one or more distally extending walls, all generally of the same thickness. In a ready state of the clip, the needle shaft of the needle cannula passes through an aperture in the back wall of the clip and against the distally extending arm of the clip, and between the arms where there are two of them, to pass into the catheter tube in order to expose the sharp tip. The needle cannula may be pulled proximally so as to bring the sharp tip within the clip proximal of the distal end walls of the arm(s), whereupon the arms close down to block distal re-emergence of the sharp tip. Also, a protuberance or other feature of the needle shaft near the sharp tip is sized not to readily pass through the back wall aperture, such that the protuberance engages against the back wall. The sharp tip is thus considered protected by the clip, which may be thought of as the locked or fired position. Any further proximal movement of the needle cannula will pull the clip out from the catheter hub.

Portions of the clip may be urged radially outwardly into engagement with an internal feature of the catheter hub so as to secure the clip within the hub. In one form, the presence of the needle against an arm (and between two of them, if present) urges an aspect of the arm(s) radially outwardly into engagement with a rib or groove of the catheter hub. In that form of clip, when the needle tip is pulled into the clip in the fired position, closing down of the arms also causes the arm aspect to move radially inwardly and away from engagement with the catheter hub, thereby releasing the clip for easy removal from the catheter hub. That form of design may be thought of as a passive tip protector, in that the user need do little m ore to remove the clip from the catheter hub than pull the sharp tip into the clip. In another form, an aspect of the clip remains urged into engagement with the catheter hub even in the fired position, such that removal thereof requires application of a force to overcome the engagement, with the force being applied by tugging the needle cannula proximally to overcome the force. The latter type of design may be thought of as an active tip protector in that the user must apply the added tugging force to overcome the hold of the clip to the catheter hub in order to remove the clip.

Clips have a disadvantage in that they tend to scrape along the needle shaft as the needle cannula is pulled proximally from the ready position to the fired position. That scraping is objectionable and can be particularly problematic in the passive tip protector due to the forces involved in the needle shaft urging the arms radially outwardly into engagement with catheter hub. In the active tip protector, the forces involved between the clip arm(s) and the needle shaft can be lessened, but at the expense, in part, of requiring higher removal forces, which can be objectionable.

A couple of recent proposals have sought to separate the catheter hub engagement function of the clip from the clip protective function so as to obtain the benefit of easy removal provided by passive tip protectors with the reduced forces on the needle shaft provided by active tip protectors. Those proposals involve an outer member about the clip, with the outer member having an engagement portion held radially outwardly into engagement with the catheter hub feature by the clip in the ready position. In those proposals, a portion of the clip is adjacent the outer member engagement portion so as to limit the ability thereof to move radially inwardly and release engagement with the catheter hub. When the needle tip is brought into the clip to place the clip in the fired position, further proximal movement of the needle cannula pulls the clip proximally relative to the outer member to misalign the clip portion from the outer member engagement portion into a release position such that the engagement portion can move radially inwardly and out of engagement with the catheter hub. These proposals thus involve a clip as an inner member and an outer member thereabout, with the two being axially shiftable from the ready and fired positions to the release position.

Those proposals seemingly provide the benefits of reduced needle shaft and clip arm forces of the active tip protectors, with the ease of removal of the passive tip protectors. But they still have drawbacks and can benefit from improvements.

SUMMARY OF INVENTION

The present invention provides safety catheters with tip protectors utilizing axially shiftable members, but which overcome drawbacks of prior proposals and improve thereon. To that end, and in accordance with a feature of the present invention, it is determined that the prior proposals required that the clip defining the inner member be partially within the axial extent of the outer member and partially exposed so as to be at least partially within the axial extent of the catheter hub distal of the outer member. In one aspect of the present invention, the tip protector has an outer member, with the engagement portion defined by one or more flexible tabs thereof which can extend radially outboard of the body of the outer member to engage the catheter hub and can move radially inwardly to release therefrom, and the inner member is sized and positioned to be completely within the axial extent of the outer member. The inner member has a portion to impede radially inward movement of the flexible tab when the inner member portion is disposed axially adjacent the flexible tab. The inner member is axially shiftable relative to the outer member between a first position wherein the distal tip, which may be a sharp tip or a blunt tip, extends distally of the tip protector and the inner member portion is disposed axially adjacent the flexible tabs so as to impede release of the outer member from the catheter hub, and a second position wherein the distal tip is within the outer member and the inner member is moved such that the inner member portion is no longer disposed axially adjacent the flexible tab such that the inner member no longer impedes release of the outer member from the catheter hub. In all positions of the inner and outer members in use, the inner member is retained completely within the axial extent of the outer member. The outer member may be in the form of a cylindrical body member, with the inner member being a multi-thickness member that defines an outer, cylindrical periphery conforming to the interior shape of the outer member cylinder.

In accordance with another feature of the present invention, it is determined that the outer member of the prior proposals were generally plastic or other elastomeric material, and thus are relatively thick. That thickness consumes some of the valuable cross-dimensional space of the catheter hub interior, and so limits the cross-dimension of the clip. In a further aspect of the invention, the outer member is a thin-walled metal body, such that there is more interior space available for the inner member. Further, in accordance with this further aspect of the invention, the inner member is advantageously not a clip, but is instead a multi-thickness plastic molded component, which can thus take advantage of the extra interior space left open by the use of the metal body outer member. The outer member may be in the form of a cylindrical body member, with the inner member defining an outer, cylindrical periphery conforming to the interior shape of the outer member cylinder.

In a particularly advantageous form of the inner plastic member, the proximal end thereof is provided with a metal washer to define the back wall aperture. As a consequence, a protuberance of the needle cannula engages with metal rather than plastic, so as to reduce the risk of deformation of the plastic which might allow the protuberance thereat to pass through the back end of the inner member.

In accordance with a still further feature of the present invention, the arms of the inner member may define on confronting faces thereof respective portions of a tapered bore, such that as the inner member is moved into the release position, and the arms come together, the tapered bore portions cooperate to define a tapered bore, or the effect of one, which narrows down to a distal portion of a passageway that is less than the diameter of the needle cannula, so as to limit distal re-emergence of the sharp tip therefrom. In a particularly advantageous form, the inner member is a multi-thickness plastic molded component which facilitates ready formation of the tapered bore portions in each arm thereof. In some forms, notably where small diameter needle cannulae are involved, the arms may also be provided with confronting ribs distal of the needle tip that mate together in the fired and/or released positions to further reduce the likelihood of distal re-emergence of the needle tip.

In accordance with yet another feature of the present invention, clips are generally prone to what is known as side-out by which the needle cannula may re-orient in the fired position so as to project the sharp tip out from between the arms along the side(s) of the clip. Some clips have been designed with free-standing wings in an effort to provide sidewalls to the clip. In accordance with a yet further aspect of the present invention, the confronting face of the arms may be provided with one or more sidebites, comprising at least one axially extending projection on the face of one of the arms, and an axially extending notch in the face of the other arm. A sidebite interengages when the inner member is in the fired (and release) position, so as to reduce the likelihood of lateral offset of the arms and/or side-out. In a particularly advantageous form, the inner member is a multi-thickness plastic member so as to facilitate formation of the sidebite(s).

In accordance with still another feature of the present invention, it is determined that the inner member can be designed with the arms being normally urged radially outwardly, so as to significantly reduce, if not wholly, eliminate the forces between the needle shaft and the inner member during movement of the needle cannula from the ready state to the fired state. In embodiments having the confronting ribs, the radially outward bias, in combination with the radial extent of the ribs, positions the ribs such that they do not touch the needle shaft in the ready position, thus further reducing the risk of forces between the needle shaft and the inner member.

By virtue of the foregoing, individually and in combination, there are thus provided safety catheters with tip protectors utilizing axially shiftable members, but which overcome drawbacks and improve on prior proposals of such tip protectors. These and other objects and advantages of the present invention shall be made apparent from the accompanying drawings and description thereof.

BRIEF DESCRIPTION OF THE DRAWINGS

The accompanying drawings, which are incorporated in and constitute a part of this specification, illustrate embodiments of the invention and, together with the general description given above and the detailed description of the embodiments given below, serve to explain the principles of the invention.

DETAILED DESCRIPTION

Figure 1:
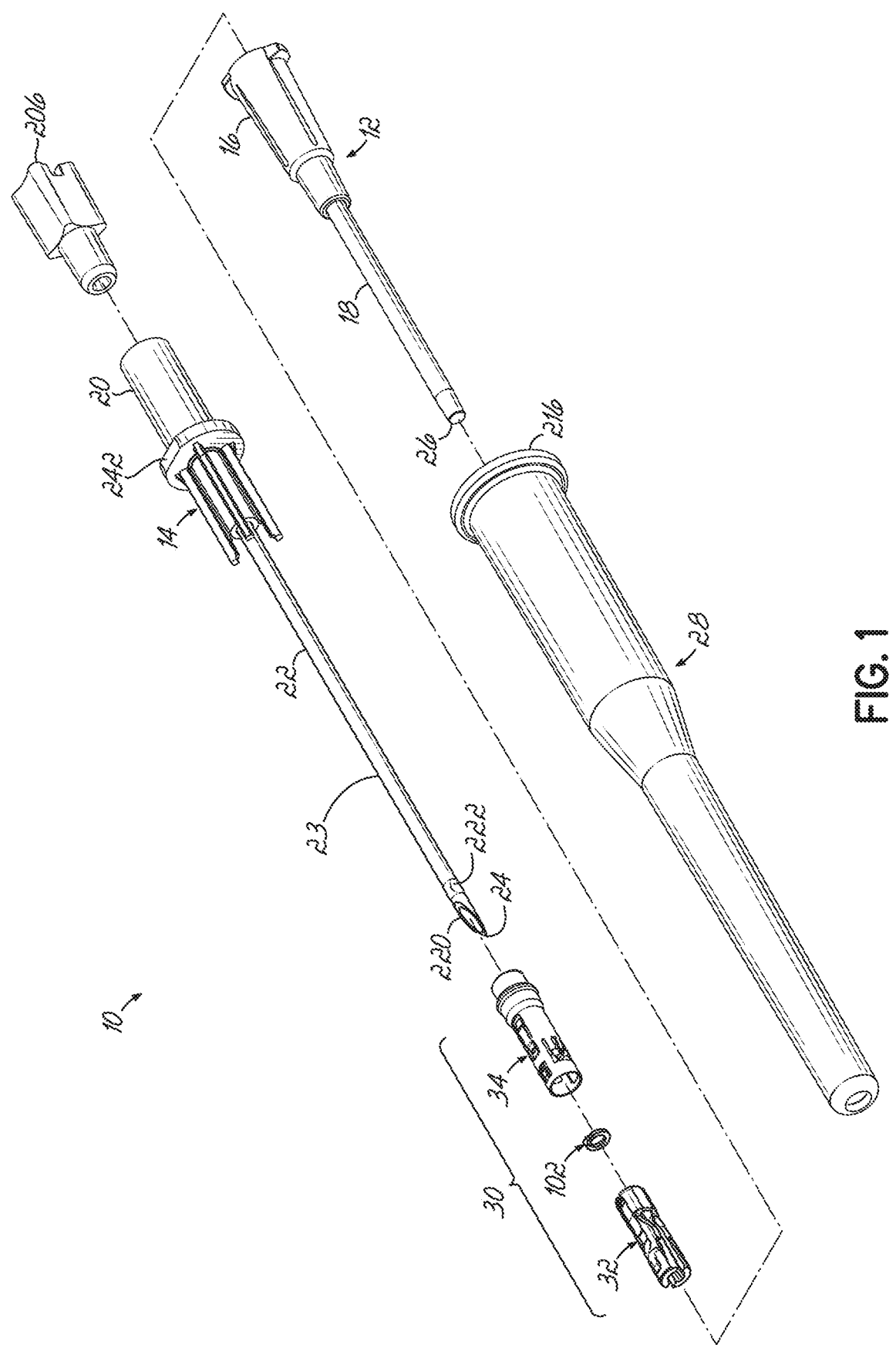
FIG. 1 is a disassembled perspective view of a safety catheter in accordance with one embodiment of the invention.
Figure 2:
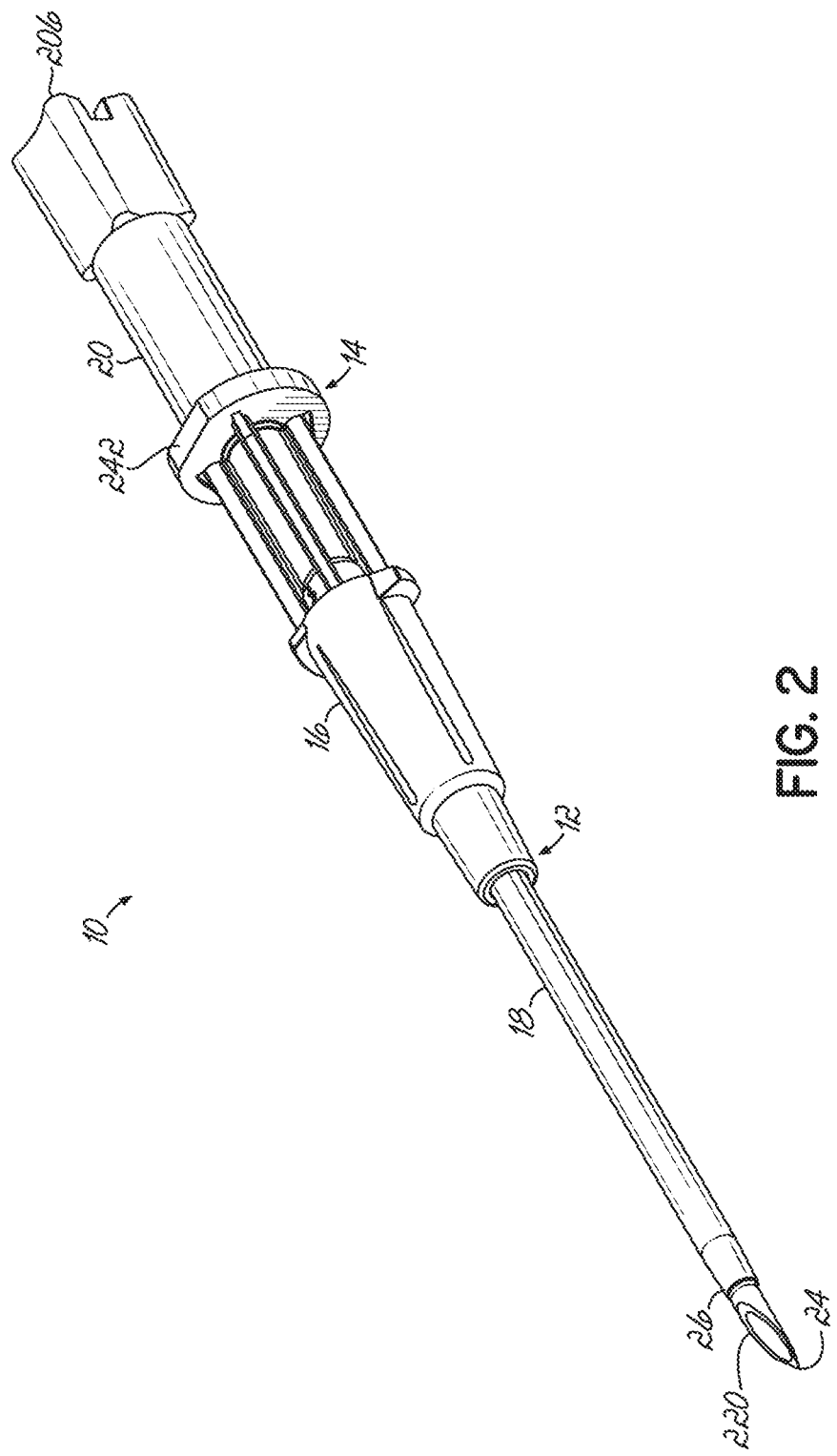
FIG. 2 is an assembled perspective view of the safety catheter shown in FIG. 1, but without the protective sheath.

In reference to FIGS. 1 and 2, a peripheral intravenous safety catheter 10 includes a catheter assembly 12 and a needle assembly 14 nested relative to the catheter assembly 12 and configured to provide an interface with the vasculature of a patient (not shown). The catheter assembly 12 includes a catheter hub 16 and a generally flexible catheter tube 18 coupled to a distal portion of the catheter hub 16 and extending distally thereof. The needle assembly 14 includes a needle support or hub 20 and a needle cannula 22 coupled to a distal portion of the needle hub 20 with a needle shaft 23 extending distally of the needle hub 20. As is generally conventional, the needle assembly 14 is positioned relative to the catheter assembly 12 such that the needle cannula 22 is disposed within the catheter tube 18 and a distal tip 24 thereof (which in the embodiment shown is sharp but could alternatively be blunt) extends beyond a distal end 26 of the catheter tube 18 in a ready position of the safety catheter 10, as illustrated in FIG. 2. A sheath 28 may be provided to protect the safety catheter 10 prior to use, such as during transit to and storage in a medical facility. As will be discussed in more detail below, safety catheter 10 includes an exemplary tip protector 30 in accordance with various aspects of the present invention configured to protect the distal tip 24 of the needle cannula 22 when the needle cannula 22 is withdrawn from the catheter hub 16 during use.

Figure 19:
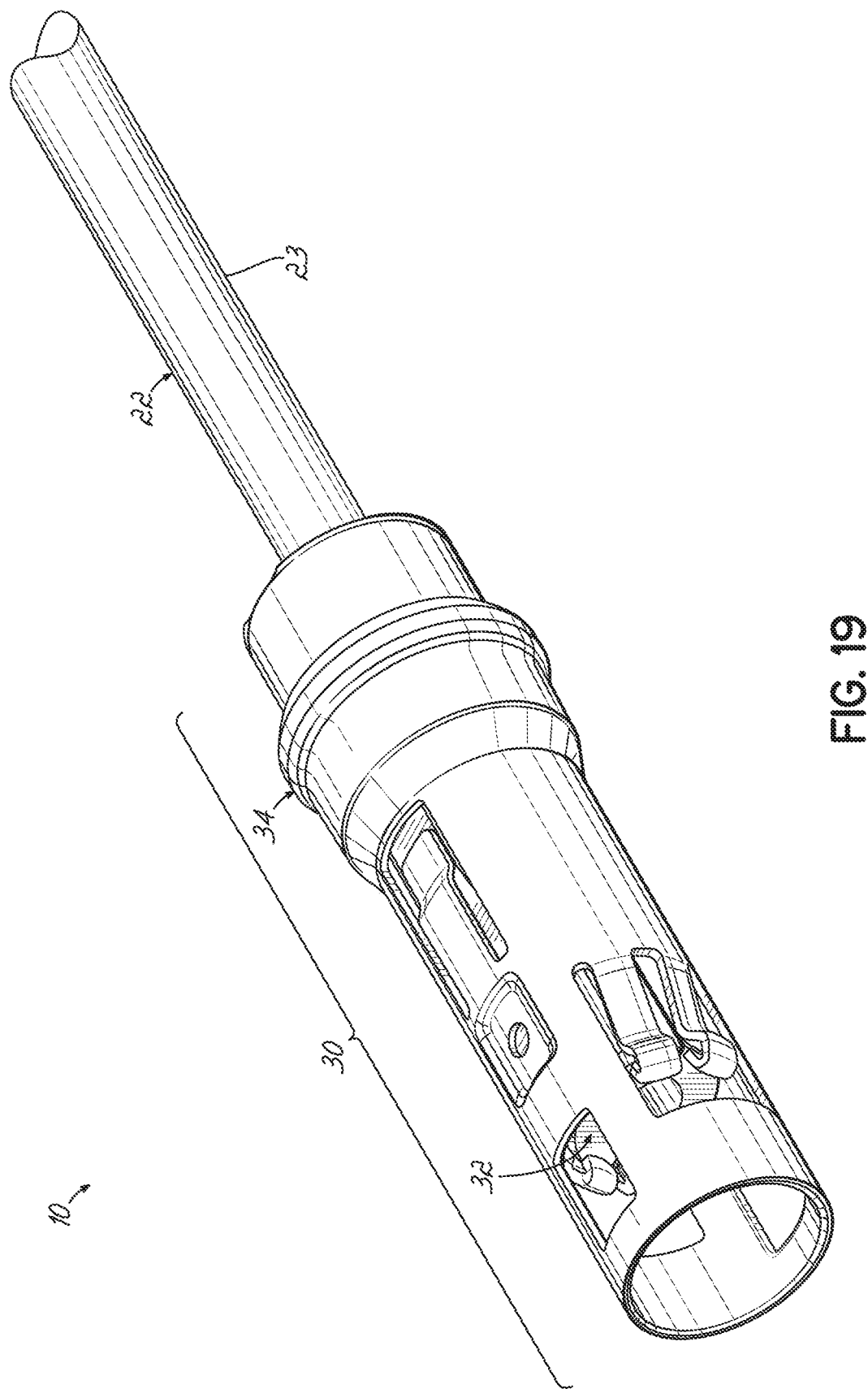
FIG. 19 is a partial perspective view of the needle assembly with the distal tip of the needle cannula shielded by the tip protector.

As illustrated in FIGS. 1 and 19, tip protector 30 is of the type configured to enclose the distal portion of the needle cannula 22, including the distal tip 24, while leaving the more proximal portions of the needle shaft 25 exposed. In accordance with one aspect of the invention, the tip protector 30 is a multi-piece design having axially shiftable members that cooperate in a manner to provide improved shielding of the distal tip 24 of the needle cannula 22, and provide improved securement/release of the tip protector 30 to and from the catheter hub 16. Additionally, as illustrated in FIG. 2, the tip protector 30 may also be of the type configured to be positioned substantially within the catheter hub 16, but as shown herein advantageously has a relatively small portion extending proximally outside thereof.

To this end, the tip protector 30 includes a first, inner member 32 received within a second, outer member 34 such that the inner member 32 is axially shiftable relative to the outer member 34 between a first position and a second position, as will be explained in more detail below. In accordance with one aspect of the invention, the inner member 32 may be designed with the primary focus of protecting or shielding the distal tip 24 of the needle cannula 22. This may be achieved, for example, by blocking the path of the needle cannula 22 once the inner m ember 32 has been axially shifted to the second position. The outer member 34, on the other hand, may be designed with the primary focus of securing and releasing the tip protector 30 to and from the catheter hub 16. While the particular functions of the tip protector 30 may be parsed out to, for example, the inner and outer members 32, 34, it should be recognized that both members 32, 34 are necessary to provide a tip protecting function in the safety catheter 10.

Figure 3:
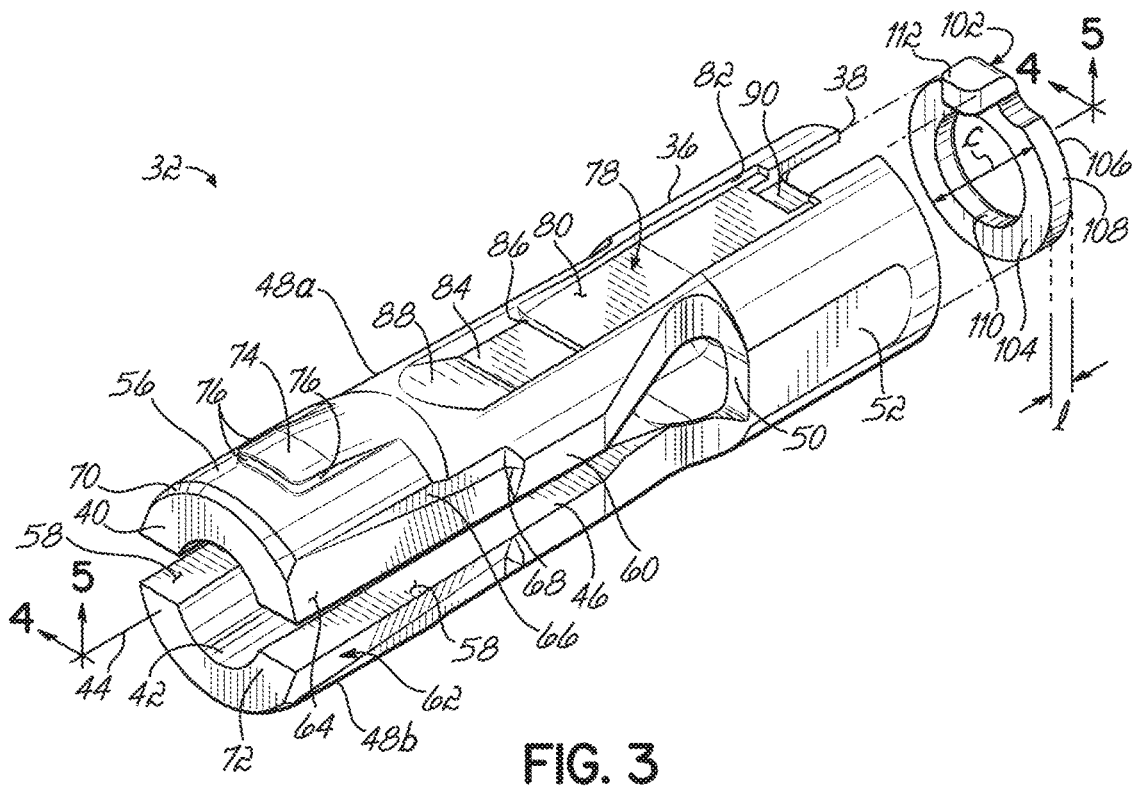
FIG. 3 is a perspective view of the inner member of the tip protector in accordance with one embodiment of the invention.
Figure 4:
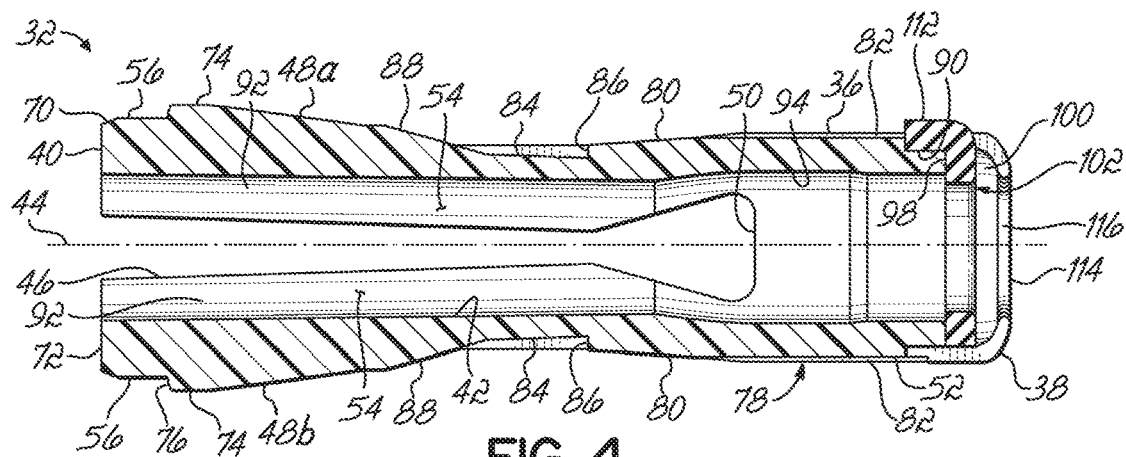
FIG. 4 is a cross-sectional view of the inner member shown in FIG. 3 taken generally along line 4-4 in FIG. 3.
Figure 5:
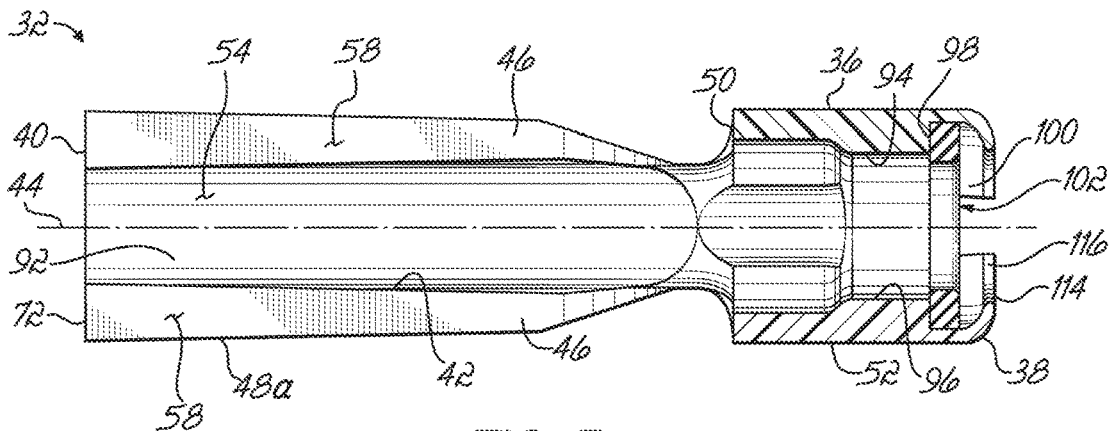
FIG. 5 is a cross-sectional view of the inner member of the tip protector taken generally along line 5-5 in FIG. 3.

In one embodiment, and as illustrated in FIGS. 3-5, the inner member 32 includes a generally cylindrical body member 36 having a proximal end 38, a distal end 40, and a passageway 42 extending between the proximal and distal ends 38, 40. Passageway 42 defines a central axis 44 and is configured to receive at least a portion of the needle cannula 22 therethrough. The cylindrical body member 36 includes a pair of opposed slots 46 formed through the wall of the body member 36 to define a pair of opposed arms 48a, 48b capable of hinging generally inward and outward relative to the central axis 44. In that regard, the slots 46 intersect the distal end 40 of the body member 36 and extend proximally therefrom. The slots 46 have a proximal end 50 that stop short of the proximal end 38 of the body member 36 to define a generally circumferentially continuous base member 52. To facilitate hinging of the arms 48a, 48b, the width of the slots 46 may vary along their length so as to, for example, increase in width adjacent to and in a direction toward the proximal end 50 of the slots 46, as shown in FIGS. 3 and 4, which operates as the hinge or pivot point for arms 48a, 48b.

In one embodiment, and although not so limited, the arms 48a, 48b may be essentially mirror images of each other, and thus a description of one of the arms (e.g., arm 48a) will suffice as a description of the other arm (arm 48b). Arm 48a includes an inner surface 54, an outer surface 56, and a pair of slot faces 58 formed by the formation of slots 46 in body member 36. The outer surface 56 may be contoured to facilitate operation of the tip protector 30. To this end, the outer surface 56 may include a first angled surface 60 adjacent each of the slot faces 58 and adjacent the proximal end 50 of the slots 46. A groove 62 may also be formed adjacent each of the slot faces 58 and includes a bottom wall 64, a side wall 66, and a proximal end wall 68 (FIG. 3). The groove 62 extends distally from the first angled surface 60 toward the distal end 40 of the arm 48a and is open along a distal end thereof. Additionally, at least a portion of the distal end 40 of the arm 48a may include a slight chamfer 70 formed in the outer surface 56 thereof which leads to a distal end face 72 of the arm 48a.

As shown in FIGS. 3 and 4, the outer surface 56 of arm 48a may include a raised ridge or boss 74 disposed adjacent the distal end 40 and along an intermediate portion of arm 48a (e.g., generally central of the two grooves 62 and, for example, about ninety degrees offset relative to slots 46). The raised boss 74 defines abutment surfaces 76, the purpose of which is described in more detail below. Moreover, arm 48a may include a second groove 78 formed along an intermediate portion of arm 48a (e.g., generally aligned with raised boss 74) that has a proximal end adjacent the proximal end 38 of body member 36, and a distal end that terminates in arm 48a proximal of raised boss 74. Groove 78 includes a bottom wall 80, and a pair of opposed side walls 82. The groove 78 may have a depth that varies along its length and may further have a cavity 84 formed in the bottom wall 80 thereof. Cavity 84 defines a first end wall 86 and a second end wall 88. In one embodiment, the first end wall 86 may generally form an acute or right angle relative to bottom wall 80, and the second end wall 88 may generally form an obtuse angle relative to the bottom wall 80. In addition to the above, the outer surface 56 of the inner member 32 may include a notch 90 formed adjacent the proximal end 38 and which extends into (e.g., recessed in) the bottom wall 80 of the groove 78.

The inner surface 54 of the inner member 32 may also be contoured to facilitate operation of the tip protector 30. As shown in FIGS. 3 and 5, the inner surface 54 of arm 48a includes a generally smooth distal tapered bore portion 92. In other words, the distal tapered bore portion 92 includes a generally defined radius of curvature that decreases in the distal direction (i.e., toward distal end 40). Collectively, the tapered bore portions 92 of both arms 48a and 48b define a tapered bore that is a portion of passageway 42 which has a first cross dimension at a first proximal location and a second cross dimension at a second distal location that is less than the first cross dimension, at least when the inner member 32 is in its second position relative to outer member 34, as explained in more detail below.

In addition to the above, an inner surface 94 of base member 52 may include an annular rib 96 that generally defines a proximal facing ledge 98. While the embodiment shown in FIGS. 3-5 illustrates a single rib that provides a continuous circumferential ledge, in alternative embodiments, multiple ribs may be utilized to provide a discontinuous ledge (not shown). The ledge 98 generally defines at least in part the boundary of a proximal cavity 100 configured to receive a needle stop member therein. As discussed in more detail below, the stop member may be configured to cooperate with the needle cannula 22 during its withdrawal from the catheter assembly 12 so as to effect relative movement between the needle cannula 22 and the tip protector 30.

In an exemplary embodiment, the stop member may include a stop washer 102 having a distal face 104, a proximal face 106, a side wall 108 extending between the distal and proximal faces 102, 104, and a central aperture 110 also extending between the distal and proximal faces 102, 104 (FIG. 3). The stop washer 102 is generally characterized by the length "l" of the side wall 108 being less than, and preferably significantly less (such as about ⅕ to ⅐) than a cross-dimension "c" (e.g., diameter or effective diameter) of the distal and proximal faces 104, 106. As also illustrated in FIG. 3, in one embodiment, the stop washer 102 may include at least one leg 112 (one shown) coupled to the side wall 108 and extending distally thereof. While the stop washer 102 is advantageous in many applications, other stop members may be used including, for example, a tubular sleeve. However, a sleeve is axially elongated as compared to a washer and may have certain drawbacks that may not be desirable in certain applications.

When the stop washer 102 is positioned within proximal cavity 100, the distal face 104 thereof is configured to engage the ledge 98 formed by the rib 96. This engagement prevents or limits distal movement of the stop washer 102 relative to the inner member 32. The stop washer 102 may be captured within cavity 100 by suitable formation of the proximal end 38 of the body member 36. To this end, the proximal end 38 includes a proximal end face 114 having an opening 116 formed therein. The opening 116 has a cross dimension (e.g., diameter) that is smaller than a cross dimension of the stop washer 102. Accordingly, the end face 114 operates to prevent or limit proximal movement of the stop washer 102 relative to the inner member 32.

In addition to the above, when the stop washer 102 is disposed within proximal cavity 100, the leg 112 is configured to be received within the notch 90 formed adjacent the proximal end 38 of the body member 36, as illustrated in FIG. 4. The purpose of the leg 112 (and thus the notch 90 that receives leg 112) is primarily directed to facilitating assembly of the safety catheter 10 through an automated manufacturing process. The leg 112 and notch 90 otherwise have no role in the proper functioning of the tip protector 30. Accordingly, those of ordinary skill in the art will realize that the leg 112 and the notch 90 that receives the leg in an assembled condition may be omitted without negatively affecting the operation of the safety catheter 10 depending on the particular requirements or preferences of an assembly process.

The body member 36 of inner member 32 may be formed from suitable materials including various metals and plastics. By way of example, the body member 36 may be formed from such materials as polypropylene, polyethylene, polyoxymethylene (acetal), polycarbonate and nylon. In one aspect, the body member 36 may be formed from plastics or other materials suitable for molding processes including, for example, various injection molding processes. In an exemplary embodiment, the inner member 32 may be formed from plastic through a molding process so as to define the multi-thickness member shown herein. The stop washer 102 may also be formed from suitable materials including various metals and plastics. The stop washer 102 may be generally more rigid than the body member 36 and advantageously may be formed from medical grade stainless steel or other metals. In this regard, the use of a more rigid material at the location of engagement between the needle cannula 22 and the inner member 32 reduces the risk of the plastic inner member from deforming and allowing the needle cannula 22 to be pulled from the tip protector 30.

The stop washer 102 may be assembled with the body member 36 during manufacturing or during a post-manufacturing process of inner member 32. By way of example, the stop washer 102 may be assembled with body member 36 in an over-molding process. In that regard, the stop washer 102 may be suitably located within a mold assembly as an insert. The mold assembly is then closed and the resin that forms the body member 36 is injected into the mold so as to form about the insert. In another embodiment, the body member 36 may be injection molded without the stop washer 102 being assembled therewith. In this method, the proximal end 38 thereof may lack the proximal end face 114 and instead be formed as an open ended tubular extension of cavity 100 (FIG. 3). Subsequent to the molding operation of body member 36, the stop washer 102 may be positioned within the cavity 100 and the proximal end 38 processed to form proximal end face 114. By way of example, a swaging or other similar process may be utilized to form the proximal end face 114. Those of ordinary skill in the art may recognize other processes for manufacturing and/or assembling the inner member 32 and aspects of the invention are not limited to those described herein.

Figure 6:
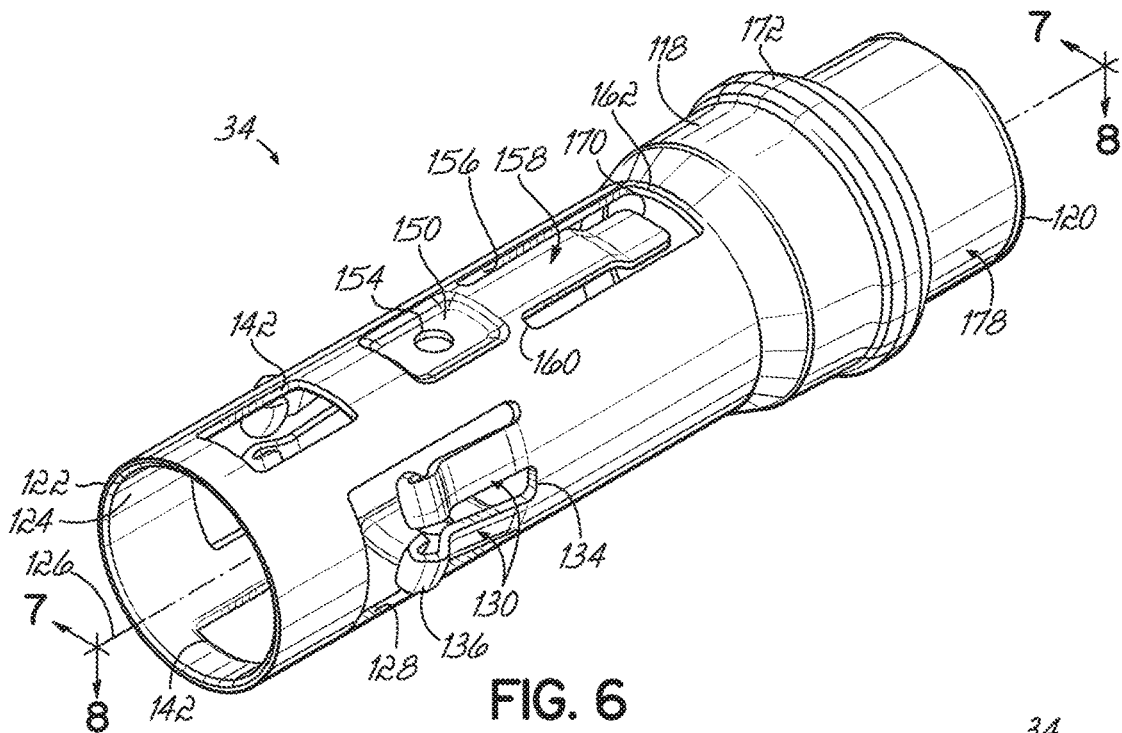
FIG. 6 is a perspective view of the outer member of the tip protector in accordance with one embodiment of the invention.
Figure 7:
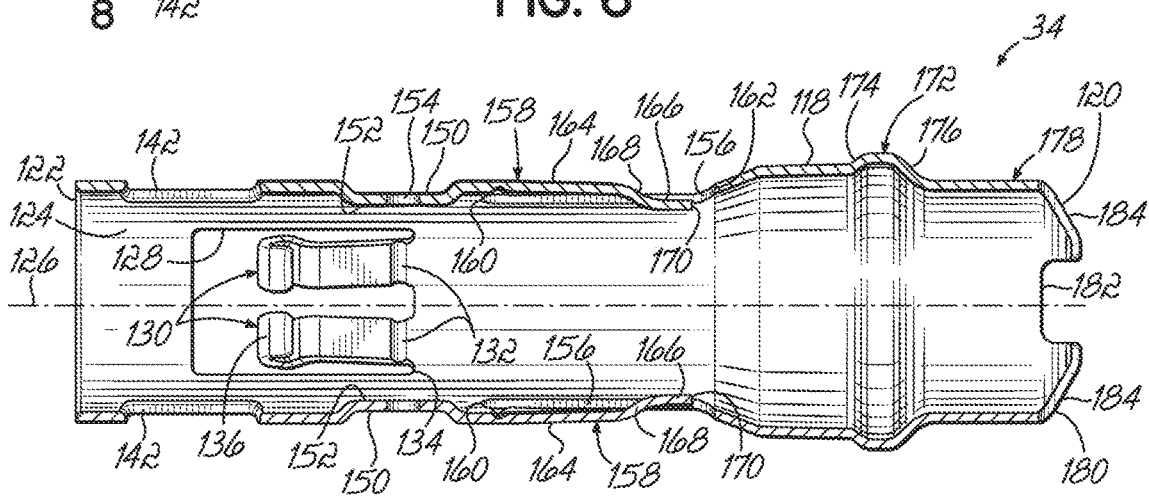
FIG. 7 is a cross-sectional view of the outer member shown in FIG. 6 taken generally along line 7-7 in FIG. 6.
Figure 8:
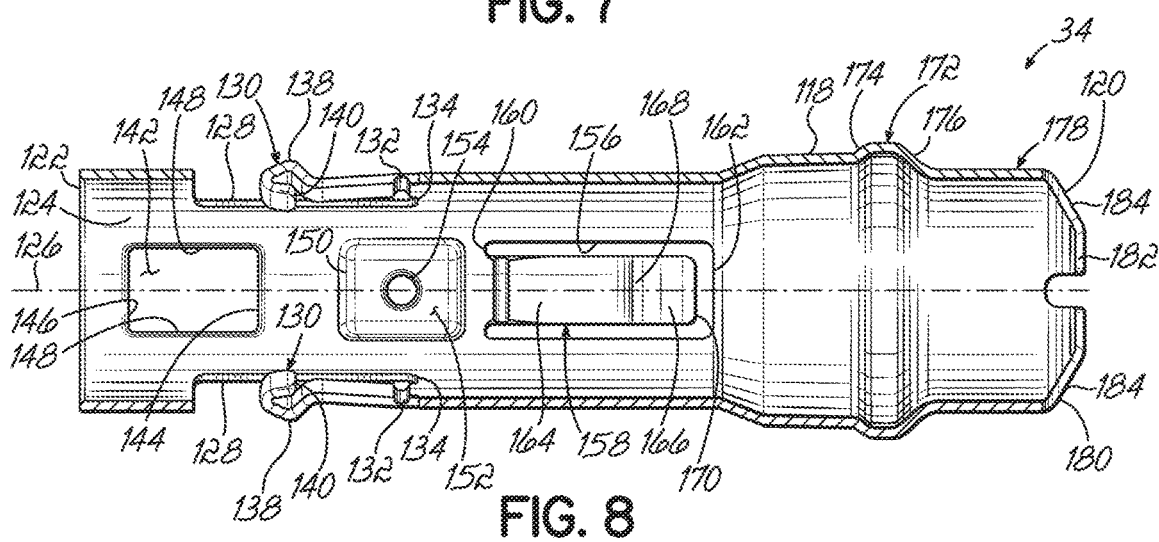
FIG. 8 is a cross-sectional view of the outer member shown in FIG. 6 taken generally along line 8-8 in FIG. 6.

Turning to the outer member 34 illustrated in FIGS. 6-8, in one embodiment, the outer member 34 includes a body member 118 which is shown here to be a thin-walled generally cylindrical body member 118. Body member 118 has a proximal end 120, a distal end 122, and a passageway 124 extending between the proximal and distal ends 120, 122. The passageway 124 defines a central axis 126 and is configured to receive at least a portion of the inner member 32 as well as at least a portion of the needle cannula 22. When the inner and outer members 32, 34 are movably coupled in the manner described below, the central axes 44, 126 may be configured to be generally colinear. Outer member 34 includes a number of features that facilitates operation of tip protector 30 through cooperation with the inner member 32 as well as with the catheter hub 16.

In that regard, cylindrical body member 118 includes a pair of opposed, generally rectangular openings or cutouts 128 formed through the wall of the body member 118 adjacent, but spaced from, the distal end 122 thereof. In one embodiment, engagement portions in the form of at least one generally flexible tab 130 may be generally disposed in one or each of the cutouts 128. For example, in one embodiment, two tabs 130 may be generally disposed in each of the cutouts 128, as shown in FIGS. 6 and 7. In an alternative embodiment, however, one tab 130 may be generally disposed in each of the cutouts 128 (not shown). In a further alternative embodiment, one or two flexible tabs 130 may be generally disposed in only one of the cutouts 128. Other combinations may also be possible. Each of the flexible tabs 130 has a J-shaped configuration with a proximal end 132 thereof coupled to a proximal end 134 of a corresponding cutout 128.

In one embodiment, a distal end 136 of the flexible tabs 130 may be curved or hooked in a generally inward direction relative to central axis 126 so as to define an abutment surface 138 on an outer surface of the tabs 130 and terminate along a contacting edge 140 inward of the abutment surface 138 (FIG. 8). While the flexible tabs 130 are shown as being curved or hooked in a generally inward direction, in an alternative embodiment, the flexible tabs 130 may be curved or hooked in a generally outward direction relative to central axis 126 such that the contacting edge 140 is directed outwardly (not shown). As will be explained in more detail below, the flexible tabs 130 may extend radially outward of the cylindrical body member 118 so as to cooperate with the catheter hub 16 and releasably secure the tip protector 30 thereto.

In addition to cutouts 128, the outer m ember 34 may include at least one, and preferably a second pair of opposed, generally rectangular openings or cutouts 142 formed through the outer wall of the body member 118 adjacent, but spaced from, the distal end 122 thereof. In one embodiment, the cutouts 142 may be about ninety degrees offset from the cutouts 128 (e.g., about central axis 126) and may be located slightly distally of cutouts 128, although not so limited. Cutouts 142 define a proximal edge 144, a distal edge 146, and a pair of side edges 148 (FIG. 8). As will be explained in more detail below, the cutouts 142 are configured to receive the raised bosses 74 on the inner member 32 when the safety catheter 10 is in the ready position.

The outer member 34 may further include at least one, and preferably a pair of opposed, generally rectangular indentations 150 formed in the outer wall of the body member 118. The indentations 150 may be generally axially aligned with cutouts 142 (e.g., about ninety degrees offset from the cutouts 128) and positioned proximally thereof. As can be appreciated, the indentations 150 formed on the outer surface of body member 118 result in projections relative to the inner surface of the body member 118 that defines engaging surfaces 152 that extend away from an inner surface and into the passageway 124 of the outer member 34. The indentations 150, in effect, define a reduced cross dimension portion of passageway 124 and are configured to cooperate with the inner member 32 in a manner to be described in more detail below. A hole 154 may be formed in at least one of the indentations 150. Similar to above, the hole 154 plays no role in the functioning of tip protector 30. Instead, hole 154 may facilitate assembly, such as providing a visual aid during the assembly process of the catheter device 10. Again, depending on the particular assembly process, the hole 154 may be omitted without negatively impacting the operation of tip protector 30.

In addition to the above, the outer member 34 may include at least one, and in an exemplary embodiment, a pair of opposed slots 156 in body member 118 which extend in a generally proximal-distal direction and are generally axially aligned with the cutouts 142 and indentations 150 of outer member 34. The slots 156, however, may be positioned generally proximally of indentations 150. A generally flexible locking tab 158 may be generally disposed in the at least one slot 156, and preferably in each of the slots 156. In that regard, the flexible locking tabs 158 may be coupled to a distal end 160 of the slots 156 and extend proximally, but stop short of the proximal end 162 of slots 156. Each of the flexible locking tabs 158 may include a distal tab portion 164, a proximal tab portion 166, and an intermediate tab portion 168. The distal tab portion 164 may be configured to generally lie within the slot 156 (e.g., within the perimeter of the outer member 34), although not so limited. The intermediate tab portion 168, however, may be generally arcuate so as to define an offset between the distal tab portion 164 and the proximal tab portion 166. In this regard, the proximal tab portion 166 may be positioned generally inward of distal tab portion 164 relative to central axis 126 of outer member 34 so as to project into passageway 124. The proximal tab portion 166 terminates in a contacting edge 170, the purpose of which is to be described in more detail below.

Adjacent the proximal end 120 of outer member 34 is a generally outwardly extending flange 172. In one embodiment, the flange 172 is circumferentially continuous (e.g., annular). In an alternative embodiment, the flange 172 may be circumferentially discontinuous and define one or more flange portions that project generally outwardly from body member 118 (not shown). Flange 172 defines a generally distally-facing lip 174 and a generally proximally-facing lip 176. As discussed in more detail below, the flange 172 may be configured to cooperate with the catheter hub 16 during use. The flange 172 may also be configured to cooperate with the needle hub 20, as discussed below. The proximal end 120 of body member 118 may further include a generally cylindrical extension portion 178 proximal of the flange 172. The extension portion 178 terminates in a generally conical proximal end face 180 having an opening 182 configured to receive at least a portion of the needle cannula 22 therethrough. In one embodiment, the proximal end face 180 may be formed by a plurality of inwardly directed tabs 184 (four shown) that define the opening 182.

The cylindrical body member 118 of outer member 34 may be formed from suitable materials including various metals and plastics. In an advantageous aspect, the body member 118 may include a thin-walled cylinder formed from sheet stock metals capable of being formed into a generally cylindrical member. Such metals include medical grade stainless steels (e.g., 410 stainless steel, 17-7 stainless steel, etc.) with or without heat treatment or other processing to achieve a suitable hardness or other desired characteristics. In an exemplary embodiment, the outer member 34 may be formed through a stamping process of the sheet stock, which stamped material is then put through a rolling process to form the outer member 34. The edges of the rolled material may then be joined through a suitable process including welding, bonding or other process. In one embodiment, the edges may include interlocking features to enhance the securement of the edges to form the cylindrical body (e.g., a zipper configuration). Those of ordinary skill in the art may recognize other processes for forming outer member 34 or for coupling the edges to form a generally cylindrical shape. In contrast to previous designs, the outer member 34 has a thin-walled (but sufficiently strong) design that provides increased space for the inner member (e.g., bulkier, plastic inner member).

Figure 9:
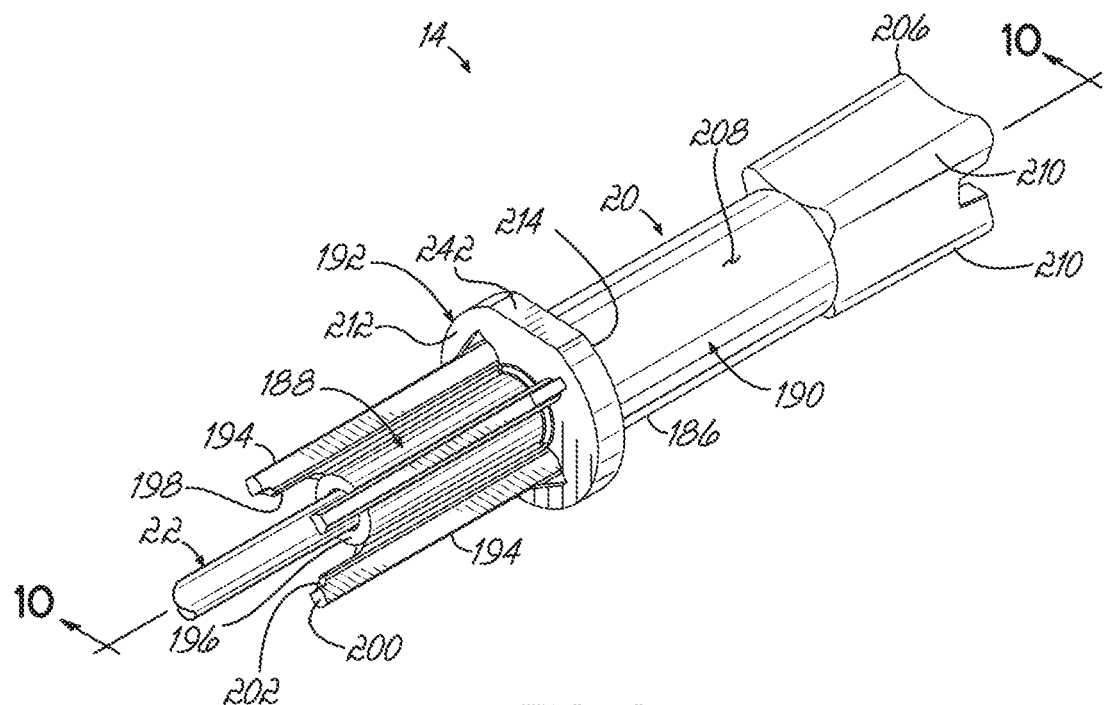
FIG. 9 is a partial perspective view of the needle assembly in accordance with one embodiment of the invention.
Figure 10:
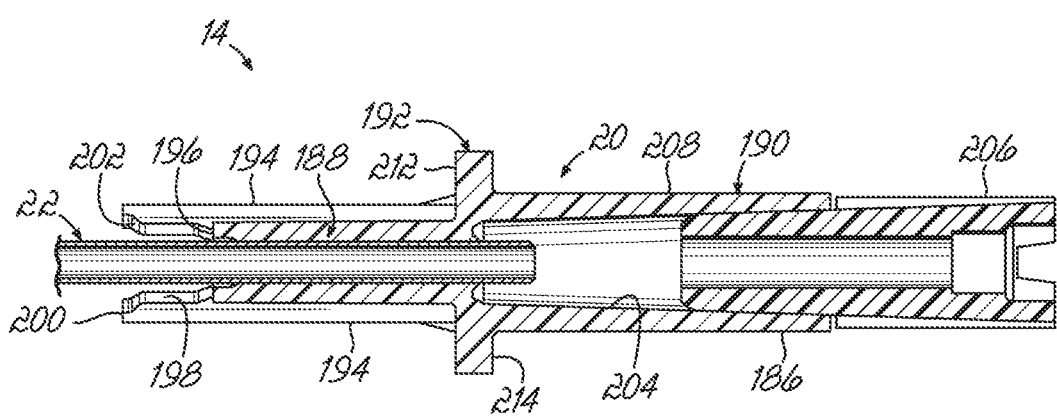
FIG. 10 is a partial cross-sectional view of the needle assembly shown in FIG. 9 taken generally along line 10-10 in FIG. 9.

As described above, the needle assembly 14 generally includes needle hub 20 and needle cannula 22 coupled to a distal portion of needle hub 20 with a needle shaft 23 extending distally thereof. As shown in more detail in FIGS. 9 and 10, the needle hub 20 may include a generally cylindrical body member 186 having a distal nose 188, a proximal tubular portion 190, and a generally outwardly extending intermediate flange 192 disposed therebetween. The distal nose 188 may be configured to receive therein and secure thereto a proximal portion of the needle cannula 22. The distal nose 188 may further include a plurality of circumferentially spaced spines 194 (four shown) that extend in a generally proximal-distal direction therealong. The spines 194 provide increased strength to the needle hub 20 and may further facilitate assembly of the safety catheter 10. At least one, and preferably each of the spines 194 extends beyond a distal end 196 of nose 188 to define an inner surface 198 and a generally distally-directed end face 200. Additionally, a distal end of inner surface 198 may include a taper or bevel 202.

The proximal tubular portion 190 defines an interior chamber 204 that is in fluid communication with a lumen of the needle cannula 22 such that the chamber 204 may operate as a flash chamber for the safety catheter 10, as is generally known in the art. A flash plug 206 closes off the chamber 204 and is configured to allow gases to pass therethrough while retaining liquid, such as blood and other bodily fluids, within chamber 204. In one embodiment, an outer surface 208 of the proximal tubular portion 190 is generally smooth. In an alternative embodiment, however, the outer surface 208 may include grip-enhancement features, such as various depressions or projections that facilitate gripping of the needle hub 20 by a user (not shown). In such a case, the ridges 210 on flash plug 206 may be oriented relative to the proximal tubular portion 190 so as to generally axially align with any such grip-enhancement features.

The intermediate flange 192 may be generally disposed between and extend generally outwardly of the distal nose 188 and the proximal tubular portion 190. In one embodiment, intermediate flange 192 may be generally disc-shaped and include a distal end face 212 and a proximal end face 214. The spines 194 on distal nose 188 may extend from distal end face 212, as shown. In one aspect, the intermediate flange 192 may be configured to cooperate with the sheath 28 that protects the safety catheter 10 during transit and storage. In that regard, the proximal opening 216 in sheath 28 (FIG. 1) may include one or more tabs (not shown) that provide a snap-fit feature between the needle hub 20 and sheath 28. More particularly, when the needle hub 20 is inserted into the sheath 28, the tabs at proximal opening 216 may be configured to engage the proximal end face 214 of intermediate flange 192 to secure the more distal portions of needle assembly 14 (and the catheter assembly 12 as well) within the sheath 28.

Figure 11:
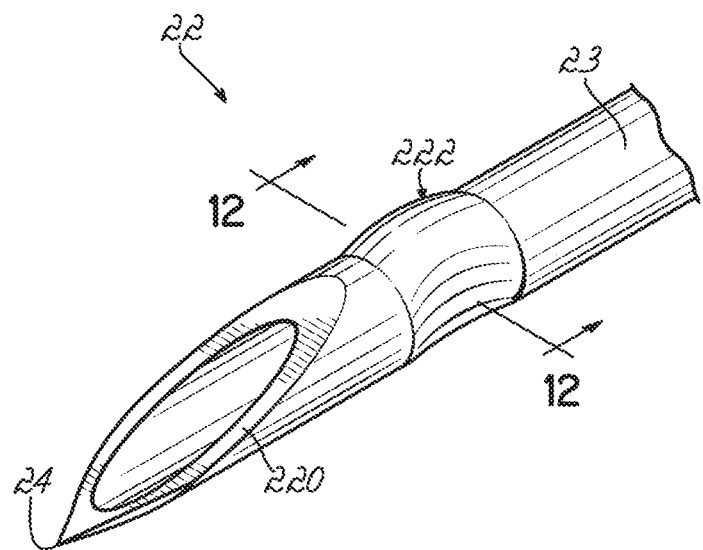
FIG. 11 is a partial perspective view of the needle cannula showing an engaging feature in accordance with one embodiment of the invention.
Figure 12:
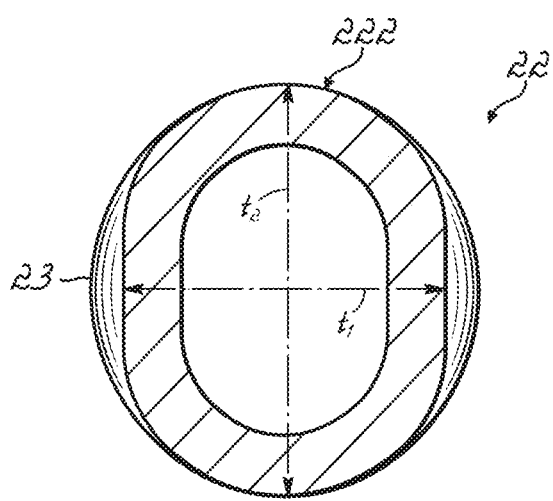
FIG. 12 is a cross-sectional view of the needle cannula shown in FIG. 11 taken generally along line 12-12 in FIG. 11.

As shown in these figures, the needle cannula 22 includes a generally straight, cylindrical and smooth needle shaft 23, a distal portion of which includes a bevel 220 that defines distal tip 24 to be sharp. The needle cannula 22 may be formed from suitable medical grade materials, such as stainless steel or other suitable materials, and the bevel 220/distal tip 24 may be formed in shaft 23 through conventional processes generally known in the art. However, as best illustrated in FIGS. 1, 11 and 12, the needle cannula 22 may include an engagement feature adjacent a distal end thereof configured to cooperate with the inner member 32 to axially shift the inner member 32 from the first position to the second position relative to the outer member 34, as discussed below. In one exemplary embodiment, the engagement feature includes a protuberance 222 adjacent a distal end of the needle cannula 22 and proximal of bevel 220.

For reasons that will become clearer below, the protuberance 222 defines a cross dimension that is greater than a cross dimension of the needle shaft 23 proximal of the protuberance 222. In one embodiment, the protuberance 222 may be formed through a pressing or pinching process. To this end, opposed pressing members (not shown) may press against the needle shaft 23 so as to generally decrease a cross dimension thereof in a first transverse direction $t_1$. As illustrated in FIG. 12, the pressing of the needle shaft 23 in the first transverse direction $t_1$ causes a corresponding bulge or increase in a cross dimension of the needle shaft 23 in a second transverse direction $t_2$, which may, for example, be about ninety degrees offset from the first transverse dimension $t_1$. The pressing process described above is only one exemplary method for forming the protuberance 222 on needle cannula 22. Those of ordinary skill in the art may recognize other processes that result in a protuberance 222 having a cross dimension that is greater than a cross dimension of the needle shaft 23 proximal thereof. The engagement feature may be integrally formed with needle cannula 22 (such as described above) or may be formed by fixing a separate element to the needle shaft 23. For example, a ring member (not shown) may be welded, bonded or otherwise secured to needle shaft 23 to form protuberance 222.

Figure 13:
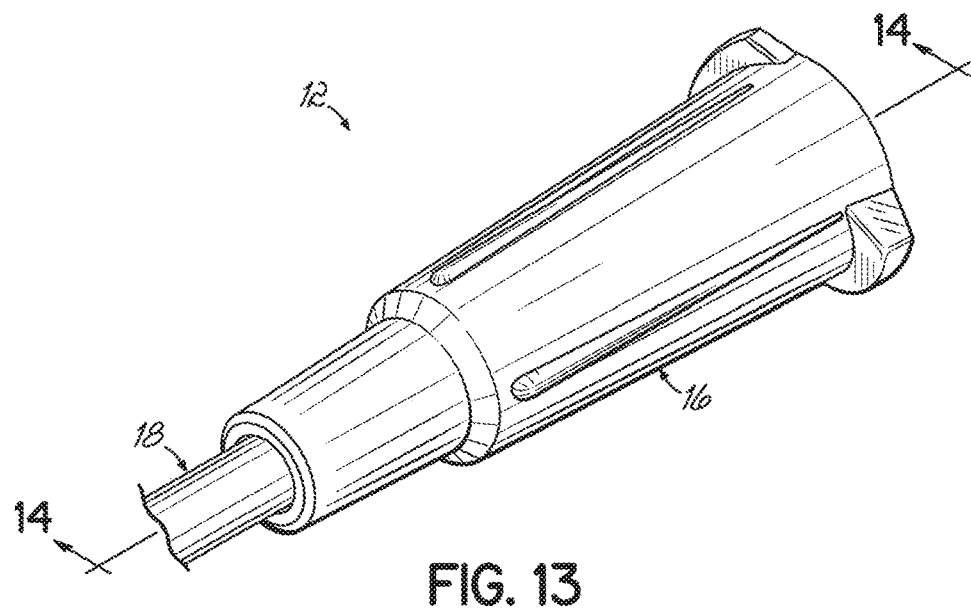
FIG. 13 is a partial perspective view of the catheter assembly in accordance with one embodiment of the invention.
Figure 14:
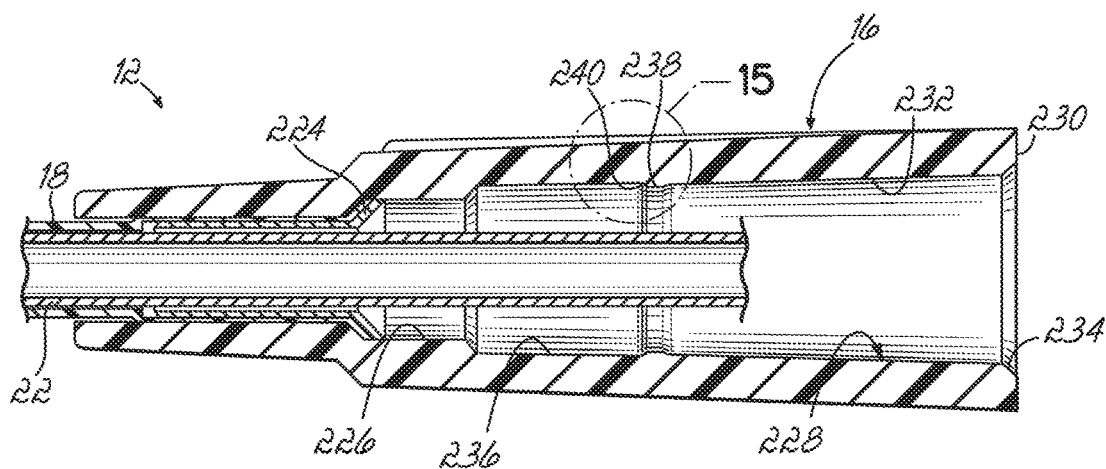
FIG. 14 is a partial cross-sectional view of the catheter assembly shown in FIG. 13 taken generally along line 14-14 in FIG. 13.
Figure 15:
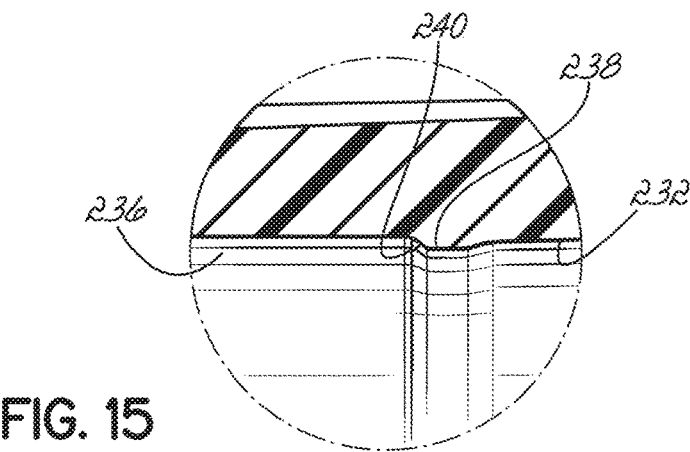
FIG. 15 is an enlarged view of the encircled portion shown in FIG. 14.

As shown in more detail in FIGS. 13-15, the catheter assembly 12 includes a catheter hub 16 and a catheter tube 18 coupled to a distal portion of catheter hub 16 and extending distally thereof. For example, as is generally known in the art, the proximal end of the catheter tube 18 may be coupled to a metal eyelet 224, which eyelet 224 is then press fit within a distal cavity 226 of the catheter hub 16. The catheter hub 16 defines a proximal cavity 228 open to the proximal end 230 thereof and having a first proximal portion 232 which may be shaped according to Luer taper standards. The first proximal portion 232 may include a bevel or chamfer 234 immediately adjacent proximal end 230. In one embodiment, the proximal cavity 228 may include a second proximal portion 236 having a generally constant cross dimension that is generally greater than (e.g., increased inner diameter) a cross dimension of the first proximal portion 232 adjacent the second proximal portion 236. The second proximal portion 236 may be defined at least in part by a transition region 238, as illustrated in FIG. 15.

As best shown in FIGS. 14 and 15, the transition region 238 defines a retention feature for releasably securing the tip protector 30 to the catheter hub 16. In one embodiment, the retention feature defines a generally outwardly extending retention groove 240 formed therein and may be circumferentially continuous (e.g., an annular groove). In an alternative embodiment, however, the groove 240 may be circumferentially discontinuous (e.g., circumferential groove segments). In still a further embodiment, the proximal cavity 228 may include a single proximal portion 232 that tapers or is otherwise shaped (according to any applicable standards) in a continuous manner from the proximal end 230 (or the end of chamfer 234) to the distal cavity 226 (e.g., no second proximal portion 236 or transition region 238) wherein the retention groove 240 is formed within the side wall of the single proximal portion 232 (not shown). Still further, the retention feature in the catheter hub 16 may have other configurations, including, for example, a circumferentially continuous or discontinuous generally inwardly extending retention rib (not shown).

With each of the elements of the safety catheter 10 described above, assembly of the safety catheter 10 will now be described in more detail. In the initial processing steps, the needle assembly 14 and catheter assembly 12 may be formed using methodologies generally known in the art. To that end, and as explained above, the proximal end of the needle cannula 22 may be press fit or otherwise coupled with the distal nose 188 of the needle hub 20, and the proximal end of the catheter tube 18 may be secured to eyelet 224, and the eyelet 224 secured within the distal cavity 226 of the catheter hub 16. The flash plug 206 may also be inserted into the proximal end of proximal tubular portion 190 of needle hub 20 so as to close off the interior chamber 204. It should be noted that as initially assembled, the needle cannula 22 does not have protuberance 222 or other engagement feature formed therein or coupled thereto.

In some applications, it may be desirable to orient the needle cannula 22 and needle hub 20 in a specific manner. By way of example, to facilitate insertion of the catheter assembly 12 into a vein or artery of a patient, the bevel 220 that defines at least in part the distal tip 24 to be sharp is generally placed in a face-up position, as illustrated in FIG. 1. In some instances, clinicians may find it difficult to orient the bevel 220 in the face-up position by visual inspection of the distal portion of the needle cannula 22. To avoid such a difficulty, the needle hub 20 may be provided with an indicator that indicates the orientation of the bevel 220 relative to the needle hub 20. In one embodiment, for example, the indicator may include a flat 242 formed on the intermediate flange 192 of the needle hub 20 that is generally axially aligned with the bevel 220 in needle cannula 22. In this way, a clinician only has to identify the flat 242 on the needle hub 20 to know the orientation of the bevel 220. It should be recognized that other indicia, including various numbers, letters, symbols, etc., may be provided as an indicator, and the invention is not limited to the flat 242 shown and described herein.

With the catheter assembly 12 and needle assembly 14 assembled, the tip protector 30 may be assembled. To this end, the inner and outer members 32, 34 may be formed separately and in a manner as described more fully above. Additionally, the stop washer 102 may be coupled to the inner member 32 in a manner as described above. Next, the inner member 32 may be loaded into the outer member 34 by inserting the proximal end 38 of the inner member 32 into the passageway 124 of the outer member 34 via its distal end 122. In one aspect, the inner and outer members 32, 34 may be oriented during this loading process. In that regard, the inner and outer members 32, 34 may be oriented such that the cutouts 142, indentations 150 and flexible tabs 158 of the outer member 34 generally axially align with the raised bosses 74 and grooves 78 formed on the inner member 32. Such an orientation also provides that the flexible tabs 130 adjacent the distal end 122 of outer member 34 generally axially align with the grooves 62 formed in the arms 48a, 48b of inner member 32. Such orienting of the inner and outer members 32, 34 is generally shown in FIG. 1.

The inner member 32 may be inserted into the outer member 34 until the proximal end 38 thereof is adjacent, but spaced from, the proximal end 120 of the outer member 34. In this regard, the inner member 32 may be partially seated within the outer member 34 and subsequently fully seated within the outer member 34. For example, in an automated assembly, it may be desirable to define a pre-assembly position wherein the inner member 32 is partially seated within the outer member 34 (e.g., during movement of the pre-assembled tip protector along the assembly line) and fully seated within the outer member in a separate assembly step. Alternatively, the inner member 32 may be fully seated within the outer member 34 without having a pre-assembly position. In any event, in this embodiment, the inner member 32 is configured to be substantially completely within the outer member 34. As noted below in an alternative embodiment, the invention is not so limited.

With the tip protector 30 assembled, the tip protector 30 may be threaded onto the needle cannula 22 by inserting the distal tip 24 thereof into the proximal end of tip protector 30 and more particularly through the proximal openings 184, 116 of the outer and inner members 34, 32, respectively. The various flexible parts of the inner and outer members 32, 34 (e.g., arms 48a, 48b, flexible tabs 130, etc.) are not being unduly constrained, such as by the outer member 34 or catheter hub 16, and therefore tip protector 30 may accommodate the insertion of the needle cannula 22 therethrough. The tip protector 30 is located on needle shaft 23 generally spaced from the distal tip 24 thereof so as to provide sufficient space for the formation of the engagement feature, such as protuberance 222. To this end, the protuberance 222 may be formed by a pressing method or other suitable methods as described above.

The catheter assembly 12 may then be loaded onto the needle assembly 14 such that the tip protector 30 is substantially positioned within the catheter hub 16, and the needle hub 20 is in proximity to the proximal end 230 thereof. In that regard, the interaction between the flexible tabs 130 and retention groove 240 may provide a snap-fit feature as the tip protector 30 is inserted into the catheter hub 16. The assembly is then loaded into the sheath 28 via its proximal opening 216 and secured together in the manner described above. The safety catheter 10 may then be further processed and appropriately packaged in a manner generally known in the art. In one embodiment and as noted above, the assembly process described above may be an automated type of process. The invention is not so limited, however, as manual or hybrid types of processes may be used for assembly of the safety catheter 10.

FIG. 2 illustrates the catheter device 10 in a ready position wherein the bevel 220 and distal tip 24 of the needle cannula 22 extend beyond the distal end 26 of the catheter tube 18, and the safety catheter 10 is ready for insertion into the vasculature of a patient. The interaction of the various components of safety catheter 10 when in the ready position will now be described in reference to FIGS. 16A and 16B. When in the ready position, a substantial portion of tip protector 30 is positioned within the catheter hub 16. In that regard, the tip protector 30 is inserted into the catheter hub 16 during assembly until the distal facing lip 174 of flange 172 engages the chamfer 234 adjacent the proximal end 230 of the catheter hub 16. This engagement prevents the tip protector 30 from moving any further distally within the catheter hub 16. In one embodiment, no portion of the tip protector 30, and more particularly, no portion of outer member 34 thereof engages the proximal end 230 of catheter hub 16. In alternative embodiments, however, the tip protector 30 may additionally or alternatively engage the proximal end 230 of catheter hub 16 (not shown). As shown in these figures, a portion of flange 172 and extension portion 178 may project beyond the proximal end 230 of catheter hub 16. The length $l_1$ of the tip protector 30 that extends proximal of the proximal end 230 is sufficiently small such that gripping and manipulating the tip protector 30 with the human hand would be, for all intents and purposes, impractical if not impossible using this portion. That portion of the outer member 34 that projects out of the catheter hub 16 is covered by the spines 194 and therefore could not be grasped in any event.

Figure 16A:
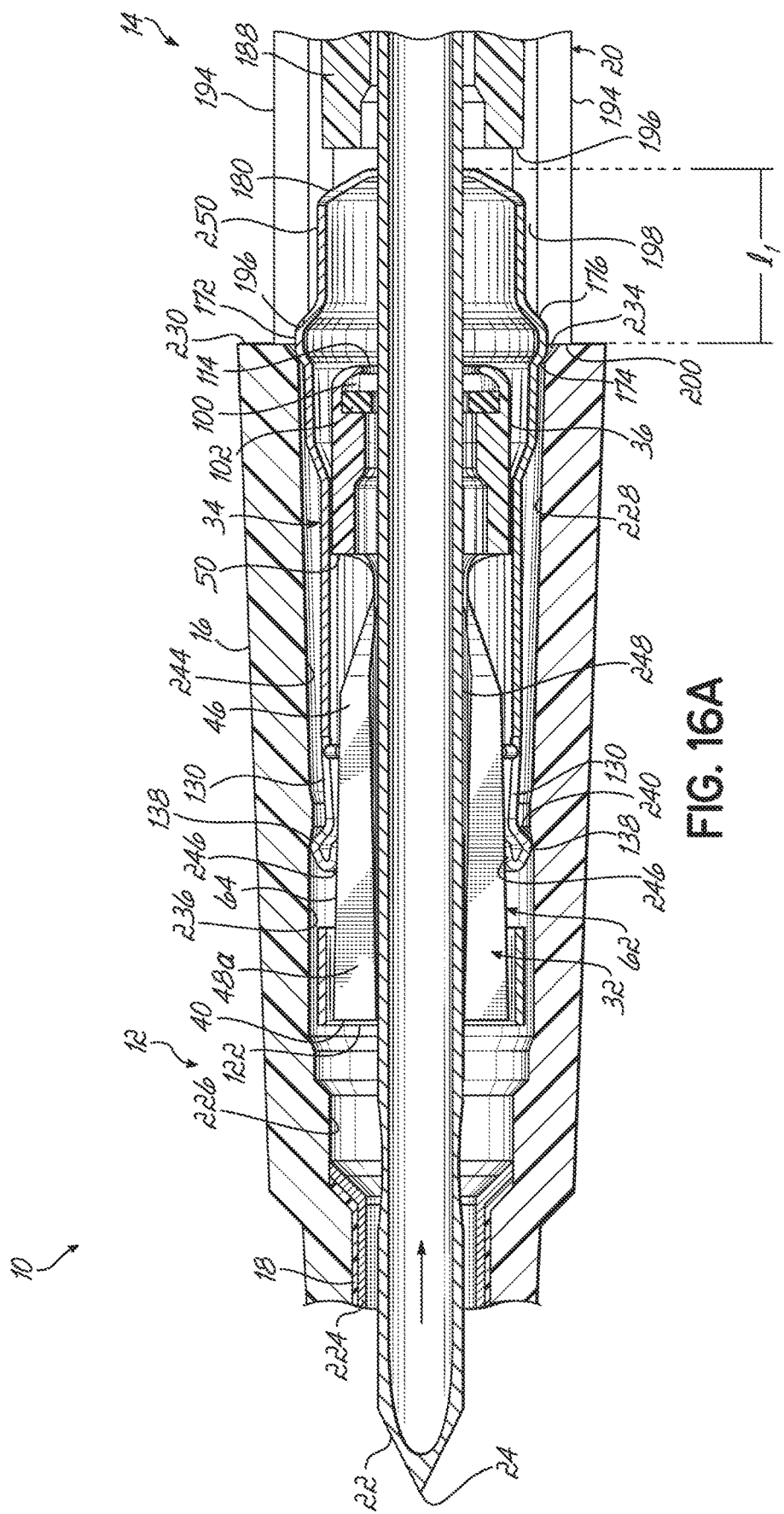
FIG. 16A is a partial cross-sectional view of the safety catheter in the ready position, wherein the inner member is in a first position relative to the outer member.

The tip protector 30 may be releasably secured within the catheter hub 16 through an interaction between the outer member 34 and the inner wall 244 of the catheter hub 16. More particularly, and as best illustrated in FIG. 16A, when in the ready position, the distal end 136 of flexible tabs 130 is positioned adjacent retention groove 240 such that the abutment surface 138 thereof is positioned within the retention groove 240. In one embodiment, the flexible tabs 130 may be configured to be biased generally inward relative to central axis 126 such that, in their natural or unbiased state (and without the inner member 32 being positioned within outer member 34), the flexible tabs 130 would extend within the passageway 124 of outer member 34.

However, due to the presence of the inner member 32 within the outer member 34, the flexible tabs 130 extend generally outward of the cylinder of the outer member 34 and against their bias when the tip protector 30 is inserted into the catheter hub 16 and in the ready position. In one embodiment, the flexible tabs 130 may be configured such that the abutment surface 138 makes contact with the inner wall 244 of the catheter hub 16 when in the ready position. Alternatively, however, the flexible tabs 130 may be configured such that the abutment surface 138 is positioned in the retention groove 240, but spaced from the inner wall 244 of the catheter hub 16. In such an embodiment, should the tip protector 30 be moved proximally away from the catheter hub 16 (i.e., should the tip protector 30 be prematurely pulled out of the catheter hub 16), the abutment surface 138 would contact the wall of the retention groove 240 and restrict further proximal movement.

While in an exemplary embodiment, the flexible tabs 130 are biased generally inwardly, in an alternative embodiment, the flexible tabs 130 may be configured to be biased generally outward relative to central axis 126 such that, in their natural or unbiased state, the flexible tabs 132 extend away from the passageway 124 of outer member 34. In this embodiment, the flexible tabs 130 may be configured such that the abutment surface 138 makes contact with the inner wall 244 of the catheter hub 16 when in the ready position. Alternatively, however, the flexible tabs 130 may be configured such that the abutment surface 138 is positioned in the retention groove 240, but spaced from the inner wall 244 of the catheter hub 16 when in the ready position. In either embodiment, such a positioning relative to the retention groove 240 is independent of the position of the inner member 32.

In reference to the exemplary embodiment, although the flexible tabs 130 are capable of moving out of retention groove 240 (e.g., under their own bias), at least when in the ready position, it should be realized that the flexible tabs 130 are impeded from moving generally radially inward (and away from retention groove 240) by the presence of a portion of the inner member 32, which is in its first position relative to outer member 34 in the ready position of catheter device 10. In that regard, as shown in FIG. 16A, when in the ready position, an inner surface 246 of the flexible tabs 130 may be in close proximity to the bottom wall 64 of grooves 62. For example, in one embodiment, the inner surface 246 of flexible tabs 130 may be configured to engage the bottom wall 64, while in an alternative embodiment, the inner surface 246 of flexible tabs 130 may be slightly spaced from the bottom wall 64. As can be appreciated, in such an alternative embodiment, the slight spacing cannot be so great as to allow the flexible tabs 130 to move out of the retention groove 240 without being impeded by the inner member 32. In the various embodiments, attempts to pull the tip protector 30 out of the catheter hub 16 would require the flexible tabs 130 to move radially inward to an extent that allows them to come away from retention groove 240. Such radially inward movement, however, is impeded due to the presence of the inner member 32 and the tip protector 30 remains secured to the catheter hub 16.

Figure 16B:
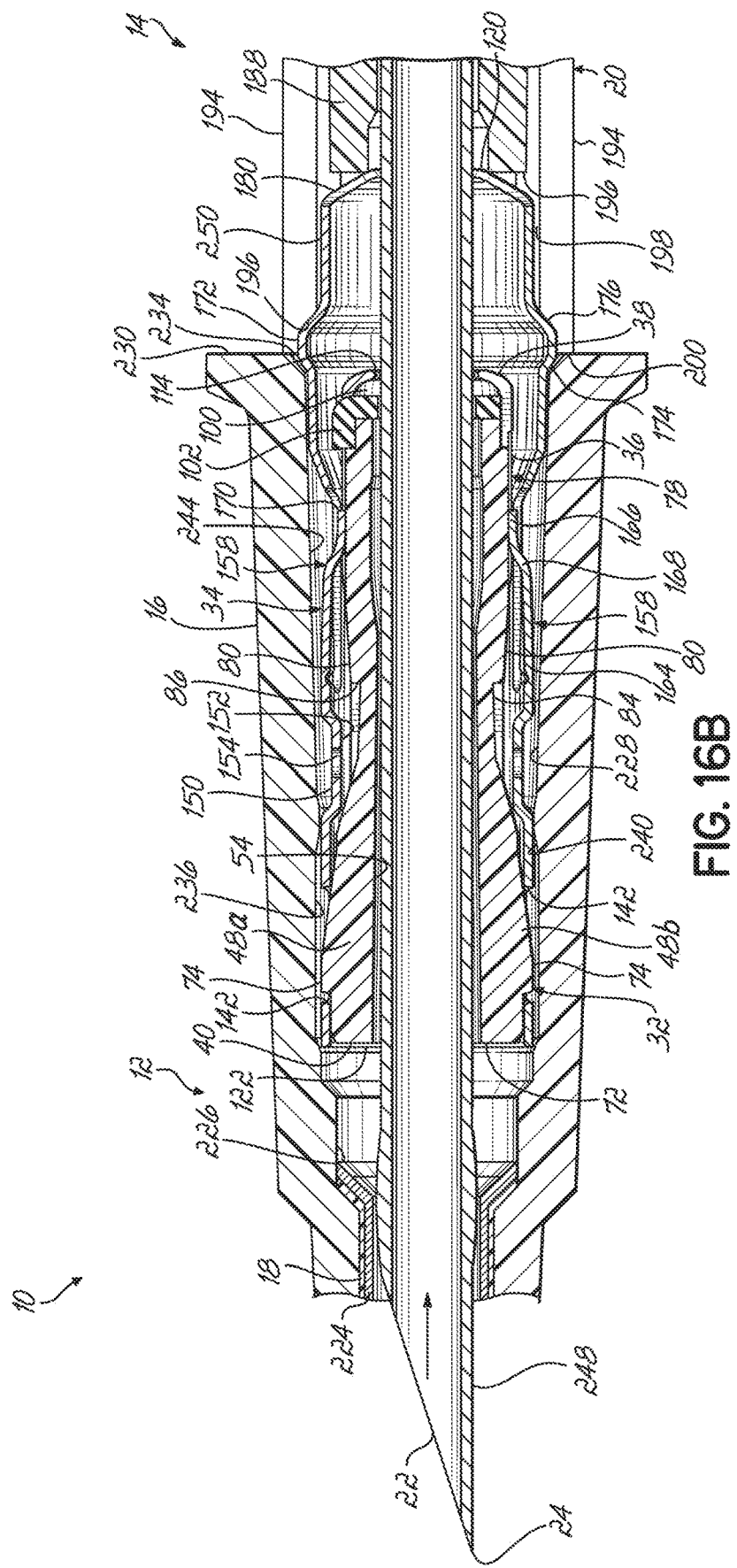
FIG. 16B is another partial cross-sectional view of the safety catheter in the ready position and 90.degree. offset from the view shown in FIG. 16A.

As further illustrated in FIGS. 16A and 16B, when in the ready position, the inner member 32 is in its first position relative to outer member 34 and is entirely positioned within the outer member 34. In one embodiment, the arms 48a, 48b may be configured to be biased generally radially outward relative to central axis 44. For example, the outer member 34 may be configured to constrain the arms 48*a*, 48*b* (i.e., but for the outer member 34, the arms 48*a*, 48*b* would move further apart from one another). When in the ready position, the inner surface 54 of the arms 48*a*, 48*b* may be in proximity to an outer surface 248 of the needle shaft 23. For example, in one embodiment, the inner surface 54 of the arms 48*a*, 48*b* may be configured to engage the outer surface 248 of the needle shaft 23. In an alternative embodiment, however, the inner surface 54 of arms 48*a*, 48*b* may be slightly spaced from the outer surface 248 of the needle shaft 23. This may, for example, provide for a reduced drag force on the needle cannula 22 as it is being pulled proximally during use.

While in one embodiment, the arms 48*a*, 48*b* are biased generally radially outward, in an alternative embodiment, the arms 48*a*, 48*b* may be configured to be biased generally radially inward relative to central axis 44. In such an embodiment, the inner surface 54 of arms 48*a*, 48*b* may be configured to engage the outer surface 248 of the needle shaft 23 and may be moved generally radially outward due to the presence of the needle cannula 22 extending through inner member 32 (e.g., the needle cannula 22 moves the arms 48*a*, 48*b* radially outward against the bias).

Additionally, the locking tabs 158 of the outer member 34 may be biased generally inward relative to central axis 126. More particularly, when in the ready position, and the inner member 32 is in its first position relative to outer member 34, the locking tabs 158 may be configured to engage the bottom wall 80 of groove 78. This engagement may serve a couple of purposes including, for example, providing a resistance force to movement of the inner member 32 relative to the outer member 34 during the initial proximal movement of the needle cannula 22 as it is being withdrawn. The engagement between the locking tabs 158 and groove 78 may further provide an anti-rotation feature between the inner and outer members 32, 34.

As discussed above, the inner and outer members 32, 34 are orientated in a specific manner during assembly so as to provide proper operation of the tip protector 30. Accordingly, it would be undesirable to have relative rotation therebetween during use of the safety catheter 10. For example, it would be undesirable to allow the inner member 32 to rotate relative to outer member 34 with rotation of the needle cannula 22. In that regard, the tip protector 30 may be designed to permit rotation of the needle cannula 22 without causing rotation of the tip protector 30 (i.e., the needle cannula 22 is free to rotate relative to the tip protector 30). Additionally, even if, through friction forces, rotation of the needle cannula 22 would tend to rotate the inner member 32 (or the outer member 34), relative rotation between the inner and outer members 32, 34 is restricted by the interaction of several features. For example, as noted above, engagement of the locking tabs 158 with grooves 78 provides a restriction to relative rotation between the inner and outer members 32, 34. More particularly, if relative rotation between the inner and outer members 32, 34 were initiated, the side edges of the flexible tabs 158 would contact the side walls 82 of grooves 78 and therefore resist the relative rotation.

Additionally, as shown in FIG. 16B, when in the ready position, the raised bosses 74 on the inner member 32 may be received within the cutouts 142 in the outer member 34 such that, for example, the outer surface of the raised bosses 74 is substantially flush with the outer surface of the outer member 34. The invention is not so limited as the raised bosses 74 may extend beyond the periphery of the outer member 34 in alternative embodiments. In any event, if relative rotation between the inner and outer members 32, 34 were initiated, the side abutment surfaces 76 of raised bosses 74 would contact the side edges 148 of cutouts 142 and therefore resist the relative rotation.

In addition to preventing relative rotation between the inner and outer members 32, 34, the raised bosses 74 and cutouts 142 may also resist axial movement of the inner member 32 relative to the outer member 34 in at least one direction. More particularly, the distal abutment surface 76 on raised bosses 74 and distal edge 146 of cutout 142 provide a positive stop that prevents the inner member 32 from axially shifting distally relative to the outer member 34 when in the ready position.

In addition to the above, the safety catheter 10 may be designed to allow the tip protector 30 to rotate relative to the catheter hub 16. However, rotation of the tip protector 30 relative to the catheter hub 16 would similarly not cause relative rotation between the inner and outer members 32, 34 due to the interaction between the features described above. Thus, in accordance with embodiments of the invention, the needle cannula 22 is free to rotate relative to the tip protector 30 and the tip protector 30, is free to rotate relative to the catheter hub 16.

As further shown in FIGS. 16A and 16B, when in the ready position, the spines 194 on needle hub 20 may be disposed about the flange 172 and extension portion 178 that extend beyond the proximal end 230 of the catheter hub 16. Additionally, in one embodiment, the end face 200 of the spines 194 may be configured to engage the proximal end 230 of the catheter hub 16. Moreover, when in the ready position, the needle hub 20 may be configured to engage or alternatively be spaced from the tip protector 30. By way of example, in one embodiment, the inner surface 198 of the spines 194 may engage the outer surface 250 of extension portion 178. Additionally, or alternatively, the taper 202 adjacent the distal end of spines 194 may engage the proximally facing lip 176 of flange 172. Furthermore, the end of distal nose 188 may additionally or alternatively engage the end face 180 of outer member 34.

After the safety catheter 10 is inserted into the artery or vein of the patient, the needle hub 20, and thus the needle cannula 22, may be moved proximally relative to the catheter assembly 12 and tip protector 30. However, the safety catheter 10 is configured such that drag forces imposed on the tip protector 30 due to the proximal movement of the needle cannula 22 are not sufficient to overcome the forces retaining the tip protector 30 to the catheter hub 16. Accordingly, the tip protector 30 remains secured to the catheter hub 16 during at least the initial proximal movement of the needle cannula 22.

Additionally, the drag forces imposed on the inner member 32 of tip protector 30 due to the proximal movement of the needle cannula 22 are not sufficient to axially shift the inner member 32 relative to the outer member 34. In this regard, the engagement between locking tabs 158 and the bottom wall 80 of grooves 78, the engagement between the flexible tabs 130 and the bottom wall 64 of grooves 62, the resistance to movement of the inner member 32 relative to the outer member 34 due to the generally outwardly biasing of the arms 48*a*, 48*b* (e.g., engagement between the raised bosses 74 on arms 48*a*, 48*b* and the proximal edge 144 of cutout 142), or other sources, provides a resistive force that is greater than the drag forces imposed on the inner member 32 due to proximal movement of the needle cannula 22. Accordingly, the inner member 32 does not move proximally relative to the outer member 34 during at least this initial proximal movement of the needle cannula 22.

Figure 17A:
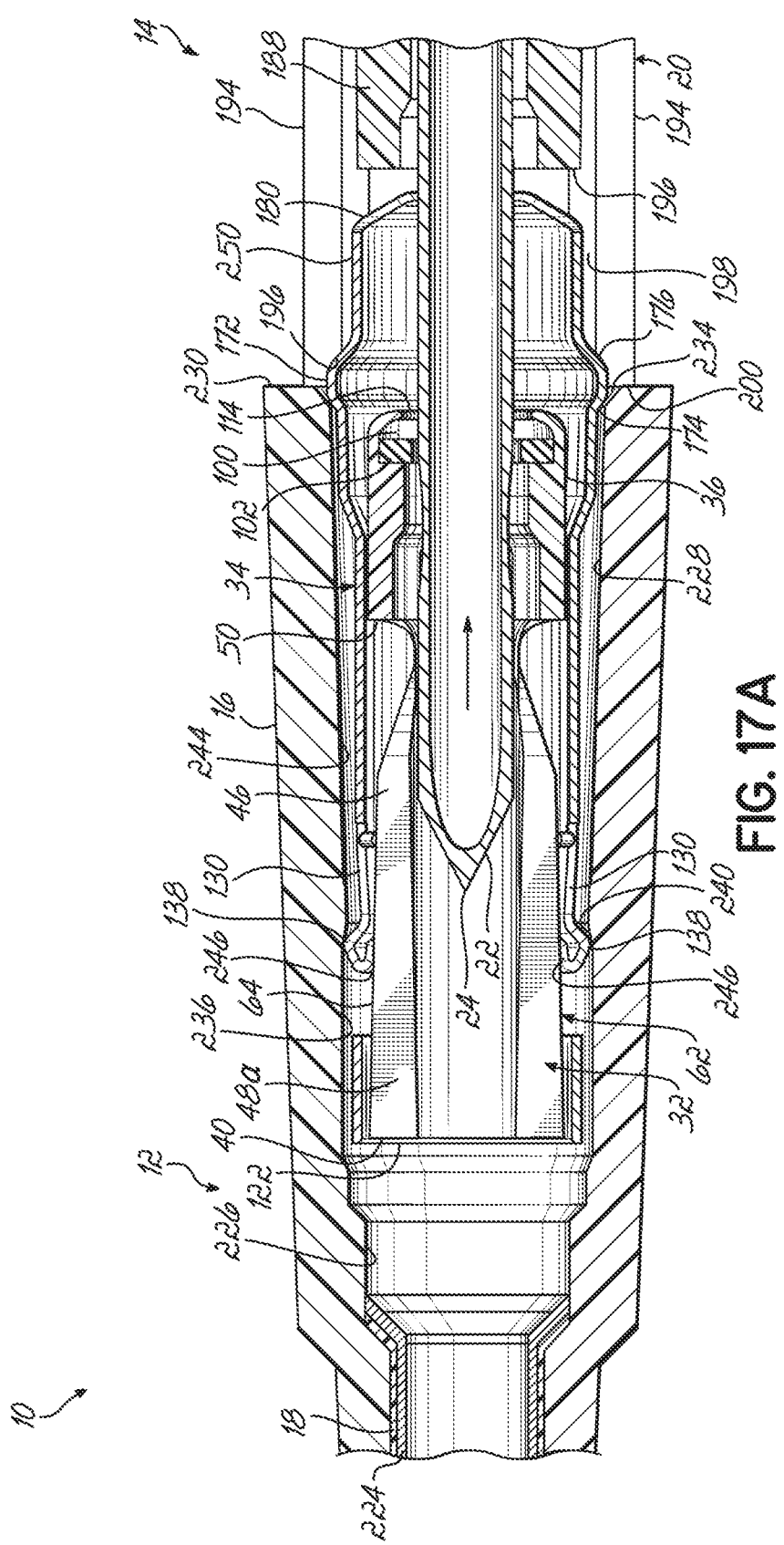
FIG. 17A is a partial cross-sectional view of the safety catheter with the distal tip of the needle cannula disposed in the tip protector.
Figure 17B:
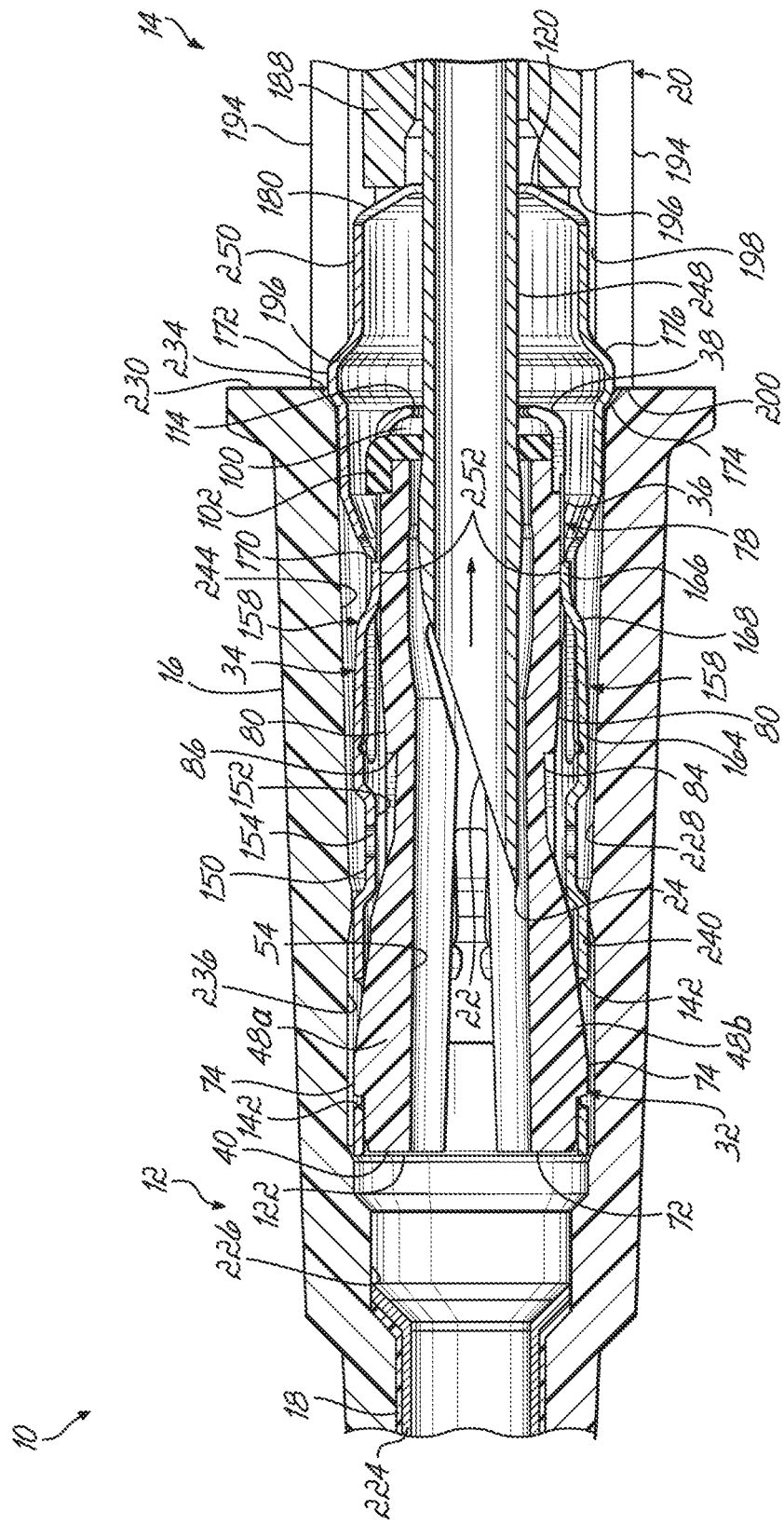
FIG. 17B is another partial cross-sectional view of the safety catheter with the distal tip of the needle cannula disposed in the tip protector and 90.degree. offset from the view shown in FIG. 17A.

As the needle hub 20 and needle cannula 22 are moved further in the proximal direction, the distal tip 24 thereof moves proximal of the distal end 122 of the outer member 34 and proximal of the distal end 40 of the inner member 32, which is disposed within the outer member 34. Such a positioning of distal tip 24 relative to inner member 32 and outer member 34 is best illustrated in FIGS. 17A and 17B. Note that although the needle cannula 22 no longer blocks the arms 48a, 48b, the arms 48a, 48b do not move radially inward (due to their outward bias). Thus, at this point, the raised bosses 74 of the inner member 32 remain in the cutouts 142 of the outer member 34. If the arms 48a, 48b were biased generally radially inward toward central axis 44, as in one of the alternative embodiments discussed above, positioning the distal tip 24 within the inner member 32 as shown in these figures would allow the arms 48a, 48b to close radially inward under their own bias due to the absence of the needle cannula 22 between the distal portion of the arms 48a, 48b. However, in such an alternative embodiment, the closing down of the arms 48a, 48b radially inward would not otherwise affect the release of the tip protector 30 from the catheter hub 16 or affect the lack of axially movement of the inner member 32 within the outer member 34.

With reference to FIGS. 17A and 17B, as the needle hub 20 and needle cannula 22 are moved further in the proximal direction, and with the distal tip 24 positioned within the inner member 32 so as to not block the radially inward movement of the arms 48a, 48b, the protuberance 222 is configured to engage the stop washer 102. In this regard, the portion of the needle shaft 23 proximal of protuberance 222 is sized so as to pass through the central aperture 110 in stop washer 102, pass through the opening 116 in the proximal end face 114 of inner member 32, and pass through the opening 182 in the proximal end face 180 of outer member 34. A cross dimension of protuberance 222, however, is sized to be greater than the cross dimension of the central aperture 110 in stop washer 102. Thus, when the protuberance 222 engages the stop washer 102, further proximal movement of the needle cannula 22 relative to the inner member 32 is thereby restricted.

Accordingly, with further proximal movement of the needle hub 20 and needle cannula 22, the engagement between the protuberance 222 and stop washer 102, which is secured within the inner member 32 as described above, causes the inner member 32 to be axially shifted proximally relative to the outer member 34. As the inner member 32 is pulled further proximally within the outer member 34, the inner surface 246 of the flexible tabs 130 remains in close proximity to (e.g., engage or be slightly spaced from) the bottom wall 64 of grooves 62. In this way, for example, even as the inner member 32 is initially axially shifted relative to the outer member 34, the presence of the inner member 32 still impedes the flexible tabs 130 from moving generally inward so as to come away from retention groove 240. Accordingly, during at least the initial axial shifting of the inner member 32 relative to the outer member 34, the outer member 34, and thus the tip protector 30, remains secured to the catheter hub 16.

In addition to the above, during at least this initial axial shifting of the inner member 32 relative to the outer member 34, an inner surface 252 of flexible tabs 158 engages and slides along the bottom wall 80 of groove 78. Additionally, during the axial shifting of the inner member 32 within the outer member 34, the cammed proximal surface of the raised bosses 74 engage the proximal edge 144 of cutouts 142 and causes the arms 48a, 48b to move generally radially inward so as to essentially close down against their bias such that the raised bosses 74 are no longer received in the cutouts 142, but are within the confines of the outer member 34 proximal of cutouts 142. Moreover, the raised bosses 74 and the indentations 150 are generally axially aligned such that the axial shifting of the inner member 32 away from its first position causes the raised bosses 74 to contact the engaging surfaces 152 of the indentations 150, which project into the passageway 124 of the outer member 34. This engagement, in turn, causes the arms 48a, 48b to close down (i.e., move radially inward toward each other) even further.

Regardless of the particular embodiment, it should be recognized that the drag forces imposed on the outer member 34 by axial shifting of the inner member 32 is less than the retentive force imposed between the outer member 34 and the catheter hub 16, such as via the retentive force imposed between the flexible tabs 130 and the retention groove 240 and the inability of the flexible tabs 130 to move away from the retention groove 240 due to the presence of the inner member 32 relative thereto. This relationship in the various forces allows the inner member 32 to be axially shifted relative to the outer member 34 without the outer member 34, and thus the tip protector 30, from being prematurely pulled proximally out of the catheter hub 16.

Figure 18A:
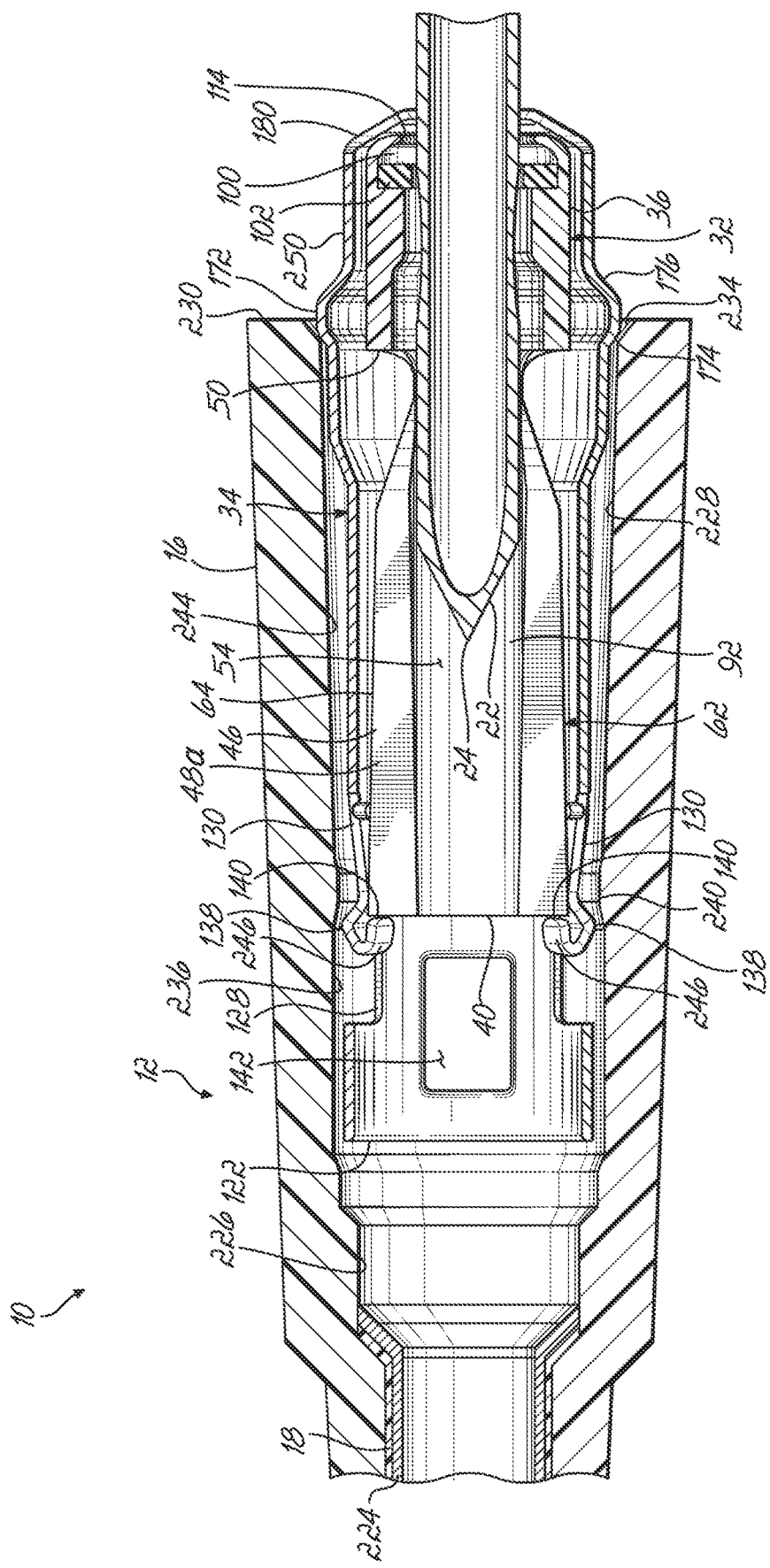
FIG. 18A is a partial cross-sectional view of the safety catheter in the protected position, wherein the inner member is in a second position relative to the outer member.
Figure 18B:
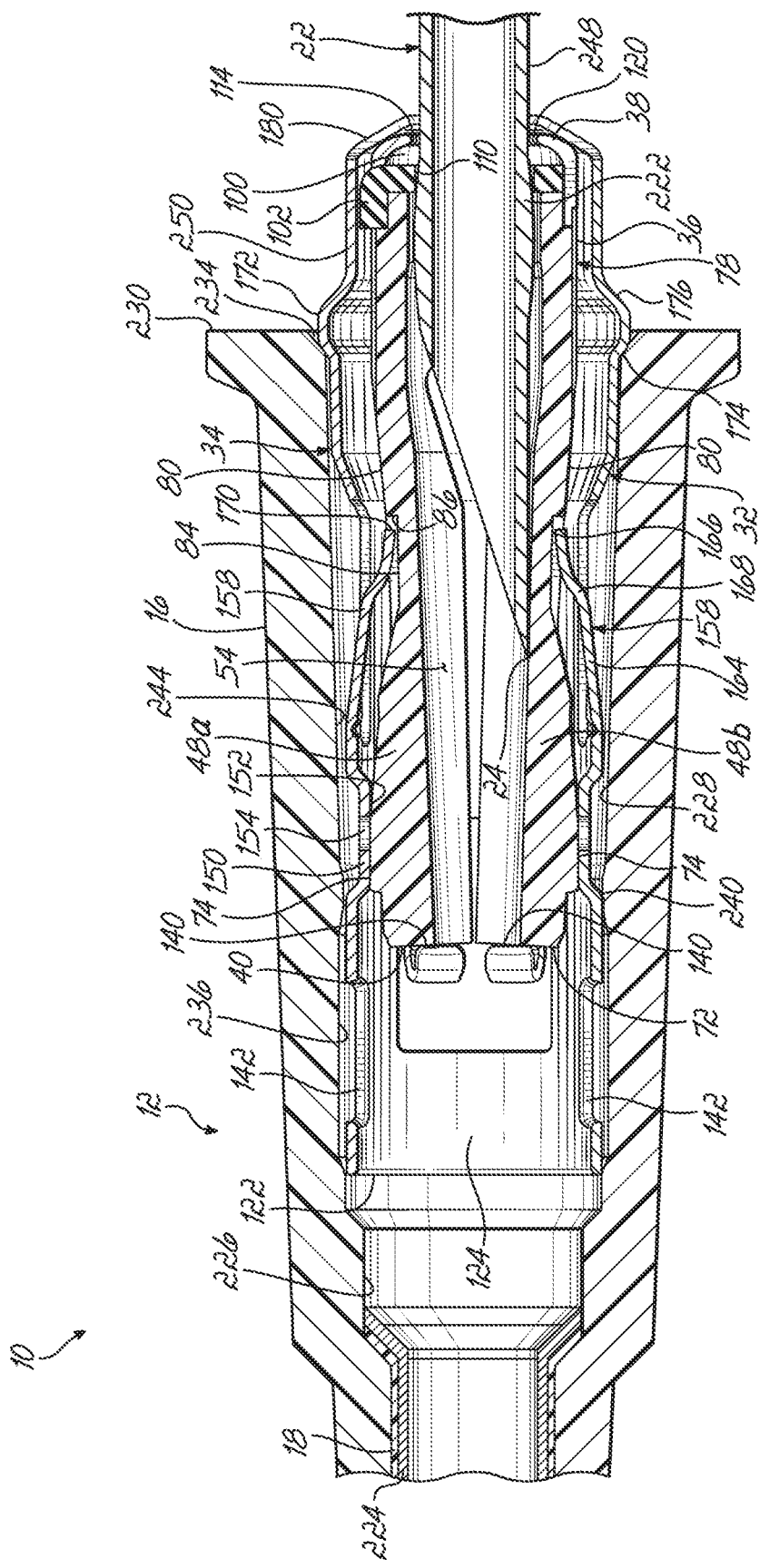
FIG. 18B is another partial cross-sectional view of the safety catheter in the protected position and 90.degree. offset from the view shown in FIG. 18A.

With reference to FIGS. 18A and 18B, as the inner member 32 continues to be axially shifted proximally within the outer member 34, the proximal tab portion 164 of locking tabs 158 drops into cavity 84 formed in the bottom wall 80 of groove 78 (FIG. 18B) due to the generally inward bias of locking tabs 158. When the proximal tab portion 164 drops into cavity 84, distal axial shifting of the inner member 32 relative to the outer member 34 is restricted by engagement between the contacting edge 170 of locking tabs 158 and the first end wall 86 of cavity 84 (i.e., the inner member 32 cannot be pushed out of the outer member 34). Furthermore, when the proximal tab portion 164 drops into cavity 84, the proximal end 38 of the inner member 32 may be in close proximity to the proximal end 120 of the outer member 34. In this regard, the opening 182 in the proximal end 120 of outer member 34 is sized so as to prevent the inner member 32 from passing therethrough.

Thus, the proximal end 120 of outer member 34 operates as a stop that prevents further proximal axial shifting of the inner member 32 relative to the outer member 34. In this way, when the proximal tab portion 164 drops into cavity 84, proximal and distal axial shifting of the inner member 32 relative to the outer member 34 is substantially restricted and the inner and outer members 32, 34 are essentially locked together. In that regard, the locking tabs 158 and cavity 84 operate as a locking mechanism that restricts axial shifting of the inner member 32 relative to the outer member 34 in the distal direction. Similarly, the sizing of opening 182 in the proximal end 120 of outer member 34, so as to block passage of inner member 32 therethrough, may also operate as a locking mechanism to restrict proximal axial shifting of the inner member 32 relative to the outer member 34.

In one embodiment, the outside surface of proximal end face 114 of inner member 32 may engage the inside surface of proximal end face 180 of outer member 34 at nearly the same time that the proximal tab portion 164 drops into cavity 84, such that there is essentially no play between the inner and outer members 32, 34 when the proximal tab portion 164 drops into cavity 84. In an alternative embodiment, however, and as illustrated in FIGS. 18A and 18B, the proximal end 38 of the inner member 32 may be slightly spaced from the proximal end 120 of the outer member 34 when the distal tab portion 164 drops into cavity 84. In such an embodiment, additional proximal axial shifting of the inner member 32 relative to the outer member 34 may be permitted before the proximal ends 38, 120 of the inner and outer members 32, 34, respectively, engage each other. In other words, although the inner and outer members 32, 34 are essentially locked together, a certain amount of play may exist between the two members 32, 34 after being locked together. In any event, the inner member 32 is positioned so as to shield the distal tip 24 of needle cannula 22.

After the proximal tab portion 164 drops into the cavity 84 (in which the proximal ends 38, 120 of the inner and outer members 32, 34 may or may not engage as explained above), the inner member 32 is in a second position relative to the outer member 34 wherein the inner member 32 no longer blocks the movement of the flexing tabs 130 radially inward due to their bias. Accordingly, when the inner member 32 is in the second position, the flexible tabs 130 are permitted to move radially inward and away from the retention groove 240 so as to release the tip protector 30 from the catheter hub 16. Although the positioning of the inner member 32 so as to no longer block the flexible tabs 130 of the outer member 34 occurs after the proximal tab portion 164 drops into the cavity 84, such positioning does not necessarily occur simultaneously.

In that regard, in one embodiment, indeed, the inner member 32 may be positioned so as to no longer block the movement of the flexible tabs 130 of the outer member 34 at substantially the same time that the proximal tab portions 164 drop into the cavity 84. In an alternative embodiment, however, the proximal tab portions 164 may drop into the cavity 84, but the inner member 32 may have an intermediate position in which it is still positioned so as to block the movement of the flexible tabs 130 away from the retention groove 240 and impede release of the tip protector 30 from the catheter hub 16. It is only with further proximal axial shifting of the inner member 32 relative to the outer member 34, and before or simultaneous with the proximal end face 114 of inner member 32 engaging the proximal end face 180 of outer member 34, that the inner member 32 is in the second position and no longer blocks the movement of the flexible tabs 130 such that the tip protector 30 may be removed from the catheter hub 16.

When the inner member 32 no longer blocks the movement of the flexible tabs 130, the tabs 130 move radially inward under their own bias and away from the retention groove 240. In one embodiment, the abutment surface 138 of the flexible tabs 130 may be completely removed from the retention groove 240 such that there is no tug force required to remove the tip protector 30 from the catheter hub 16 (e.g., passive release). In this embodiment, the flexible tabs 130 may move radially inward such that at least a portion of the tabs 130 drop in front of the inner member 32. More particularly, the contacting edge 140 of the tabs 130 may engage or confront (e.g., be slightly spaced from) the distal end face 72 of the inner member 32, when the inner member 32 no longer blocks the tabs 130.

In an alternative embodiment, the flexible tabs 130 may move radially inward under their own bias when no longer blocked by the inner member 32, but by an amount that does not completely remove the abutment surface 138 from the retention groove 240. In this embodiment, when the tip protector 30 is removed from the catheter hub 16, the abutment surface 138 will slightly contact the retention groove 240 causing the flexible tabs 130 to move slightly radially inward and out of the retention groove 240. This will result in a relatively small tug force in order to remove the tip protector 30 from the catheter hub 16.

While the operation has been described above for the flexible tabs 130 being biased generally radially inward relative to central axis 126, one of ordinary skill in the art will readily understand operation of the tip protector 30 when the flexible tabs 130 are biased generally radially outward relative to central axis 126. In this regard, one of the primary differences is that when the inner member 32 is in its second position and no longer blocking the movement of the tabs 130, the tabs 130 will not move radially inward under a biasing force and away from the retention groove 240 (as was the case above). Instead, the abutment surface 138 will remain engaged or nearly engaged with the retention groove 240. Similar to the above, in this embodiment, when the tip protector 30 is removed from the catheter hub 16, the abutment surface 138 will contact the retention groove 240 causing the flexible tabs 130 to move radially inward and out of the retention groove 240 (e.g., duckbill type). As the flexible tabs 130 are more fully positioned relative to the retention groove 240, a larger tug force may be required in order to remove the tip protector 30 from the catheter hub 16 (e.g., active release). In some applications, such a tug force may be undesirable in which case the embodiment having radially inward biased flexible tabs 130 may be employed.

FIG. 19 illustrates the needle assembly 14 fully withdrawn from the catheter assembly 12 (not shown), which remains in fluid communication with the vasculature of the patient. As shown, the distal portion of the needle cannula 22, including the distal tip 24 thereof, is shielded by tip protector 30 while more proximal portions of the needle shaft 23 are exposed. Furthermore, the tip protector 30 is designed to prevent or significantly reduce the chance or likelihood of re-exposing the distal tip 24 of the needle cannula 22. As discussed above, once the locking tabs 158 drop into cavity 80, the inner and outer members 32, 34 are essentially locked together and tip protector 30 is also essentially locked onto needle cannula 22. In that regard, should the needle cannula 22 be pulled proximally relative to the tip protector 30 (e.g., such as by grabbing the outer member 34 thereof with one hand and pulling proximally on the needle hub 20 with the outer hand), the protuberance 222 will act on stop washer 102, which in turn acts on inner member 32. However, as noted above, the proximal end 38 of inner member 32 is engaged with or is in near engagement with the proximal end 120 of outer member 34 so as to effectively prevent the needle cannula 22 from being pulled proximally out of the tip protector 30.

Similarly, should the needle cannula 22 be pushed distally relative to the tip protector 30 (e.g., such as by grabbing the outer member 34 thereof with one hand and pushing distally on the needle hub 20 with the outer hand), there may be some slight distal movement of the needle cannula 22 relative to tip protector 30. However, with reference to FIGS. 18A and 18B, as the needle cannula 22 moves distally, the needle cannula 22 will contact the inner surface 54 of arms 48a, 48b. More particularly, when the inner member 32 is in its second position relative to the outer member 34, the cross dimension of passageway 42 along a distal portion thereof is smaller than the cross dimension of the needle shaft 23 adjacent the distal tip 24. Accordingly, when in the second position, the passageway 42 along distal tapered bore portions 92 is sized so as to block the path of needle cannula 22 (i.e., the size of the distal tapered bore is smaller than the needle cannula 22). Additionally, when in the second position, the arms 48a, 48b of inner member 32 are constrained by the outer member 34 (e.g., engagement between the engaging surfaces 152 of indentations 150 and the raised bosses 74), and thus, the arms 48a, 48b are not capable of flexing generally radially outward so as to increase the size of passageway 42 and allowing the needle cannula 22 to pass therethrough.

Furthermore, when distal movement of the needle cannula 22 relative to the inner member 32 has been blocked, depending on the particular embodiment, it may be possible to axially shift the inner member 32 distally relative to the outer member 34. For example, if there is some slight play between the inner and outer members 32, 34 when they are essentially locked together, such relative axial shifting therebetween may be possible. However, any such relative axial shifting is small and distal movement of the inner member 32 relative to the outer member 34 is eventually restricted by engagement of the contacting edge 170 of locking tabs 158 and the first end wall 86 of cavity 84. Accordingly, even though there may be slight relative movement between the needle cannula 22 and tip protector 30, ultimately the distal tip 24 of the needle cannula 22 is effectively prevented from re-emerging by pushing the needle cannula 22 distally out of the tip protector 30.

Figure 20:
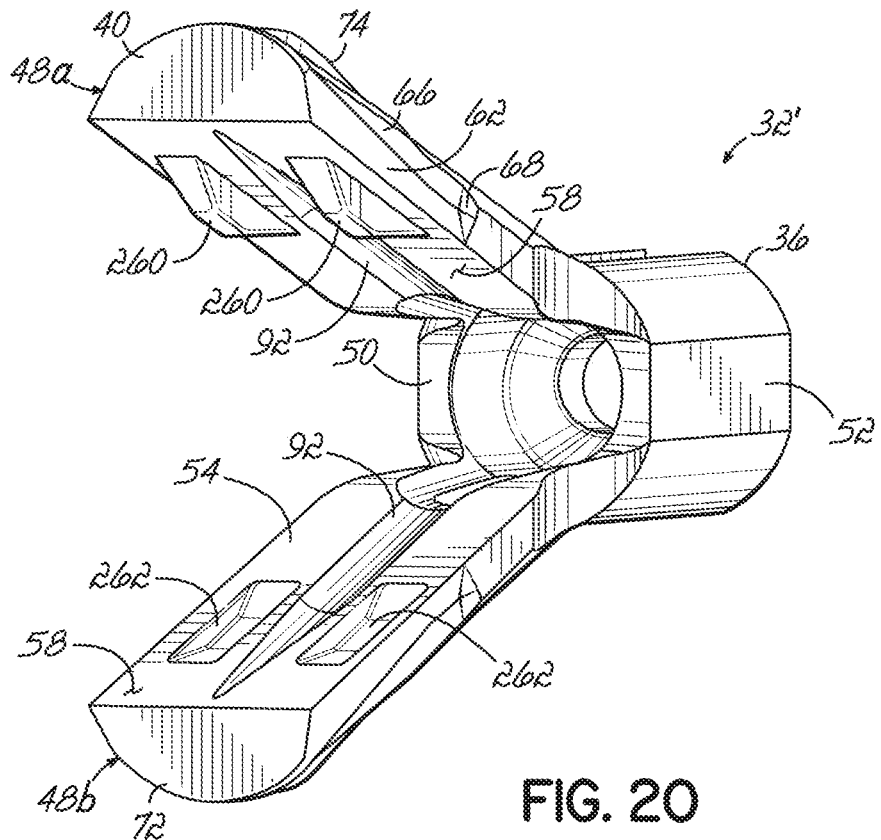
FIG. 20 is a perspective view of an inner member of the tip protector in an alternative embodiment in accordance with the invention.

In various alternative embodiments, the inner member may include additional features to restrict re-emergence of the needle cannula 22 by pushing the needle cannula 22 distally out of the tip protector 30. By way of example, when the cross dimension of the needle shaft 23 becomes relatively small (e.g., 20, 22, and 24 gauge cannulas), the needle cannula 22 may be more susceptible to undesirable flexing and a possible side-out failure mode. Accordingly, for these larger gauges, it may be desirable to include features that limit or restrict the amount of flexing of the needle cannula 22 during, for example, a potential side-out failure mode or other accidental or extreme conditions. To this end and as illustrated in FIG. 20, the inner m ember 32' may include sidebites. More particularly, the sidebites may include one or more projections 260 on the inner surface 54 of at least one the arms 48a, 48b that limit the flexing of the needle cannula 22. In an exemplary embodiment, at least one of the arms 48a, 48b includes a projection 260 disposed on opposed sides of the tapered bore portion 92, such as along slot faces 58, which are increased due to the smaller size of tapered bore portion 92. These projections 260 essentially block excessive flexing of the needle cannula 22 in a direction toward the opposed slots 46. In one embodiment, the sidebites may be integrally formed in the inner member 32' such as, for example, during molding of the inner member 32'.

In order to allow the arms 48a, 48b of the inner member 32' to move to a fully closed position (such as when in the second position), the arms 48a, 48b, which opposes the projections 260 may include a corresponding notch 262 configured to receive at least a portion of the projections 260 therein. In an exemplary embodiment, these may also be formed during molding of the inner member 32'. In this way, the operation of the tip protector 30 is not adversely effected while providing an additional feature for restricting re-emergence of the needle cannula 22 in a potential failure mode or extreme condition. In any event, should the needle cannula 22 be forced distally relative to the tip protector 30 and the needle cannula 22 start bending or flexing in a direction toward the opposed slots 46, the needle cannula 22 will contact the projections 260 and be prevented from any further flexing in those directions. Of course, any flexing or bending of the needle cannula 22 in directions other than toward the opposed slots 46 would be restricted by engagement with the solid inner surface 54 arms 48a, 48b themselves.

Figure 21:
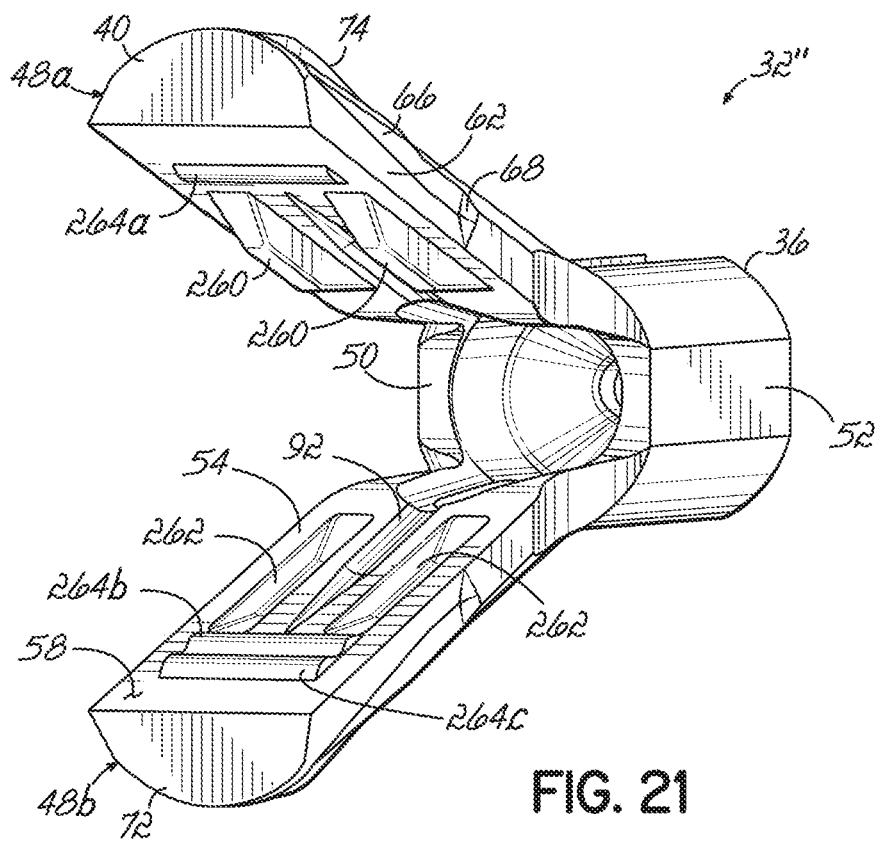
FIG. 21 is a perspective view of an inner member of the tip protector in a further alternative embodiment in accordance with the invention.
Figure 22A:
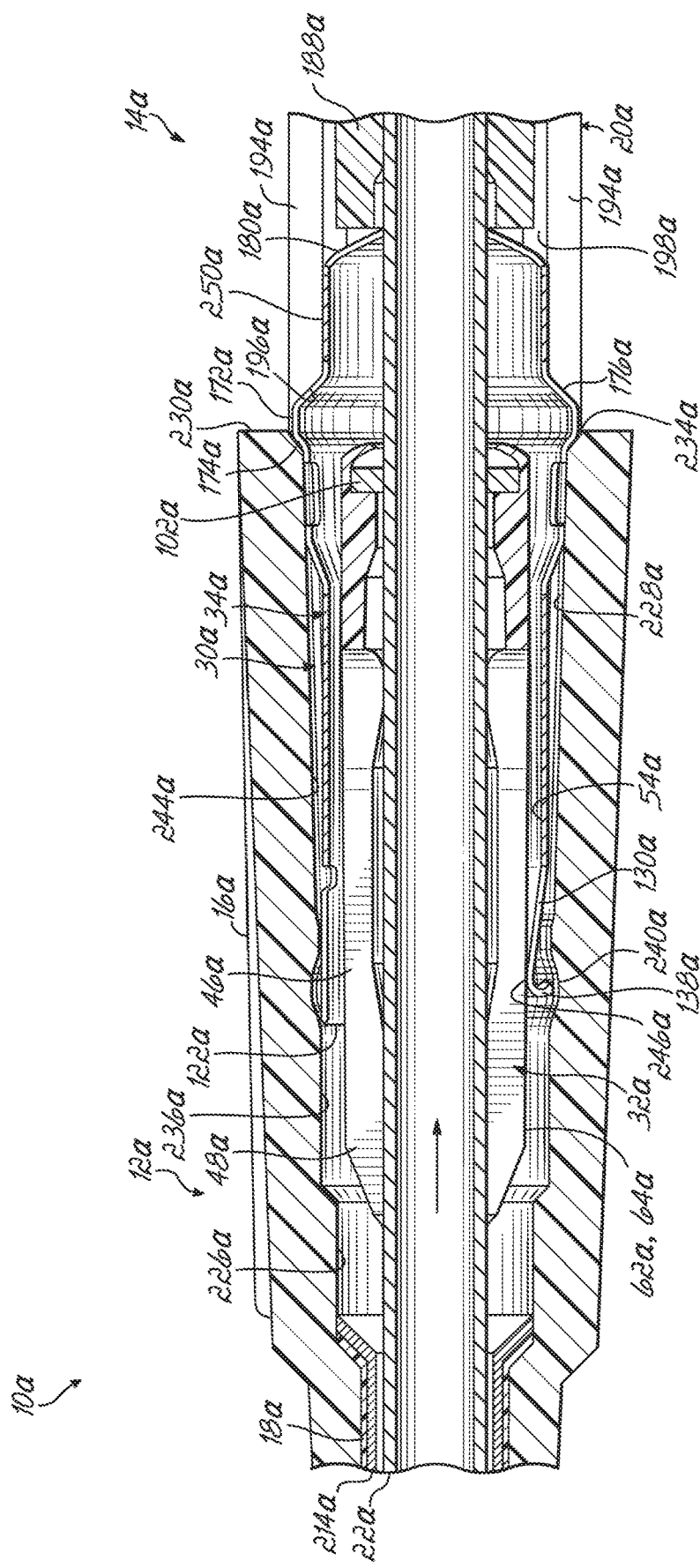
FIG. 22A is a partial cross-sectional view of an alternative embodiment of a safety catheter in the ready position, wherein the inner member is in a first position relative to the outer member.
Figure 22B:
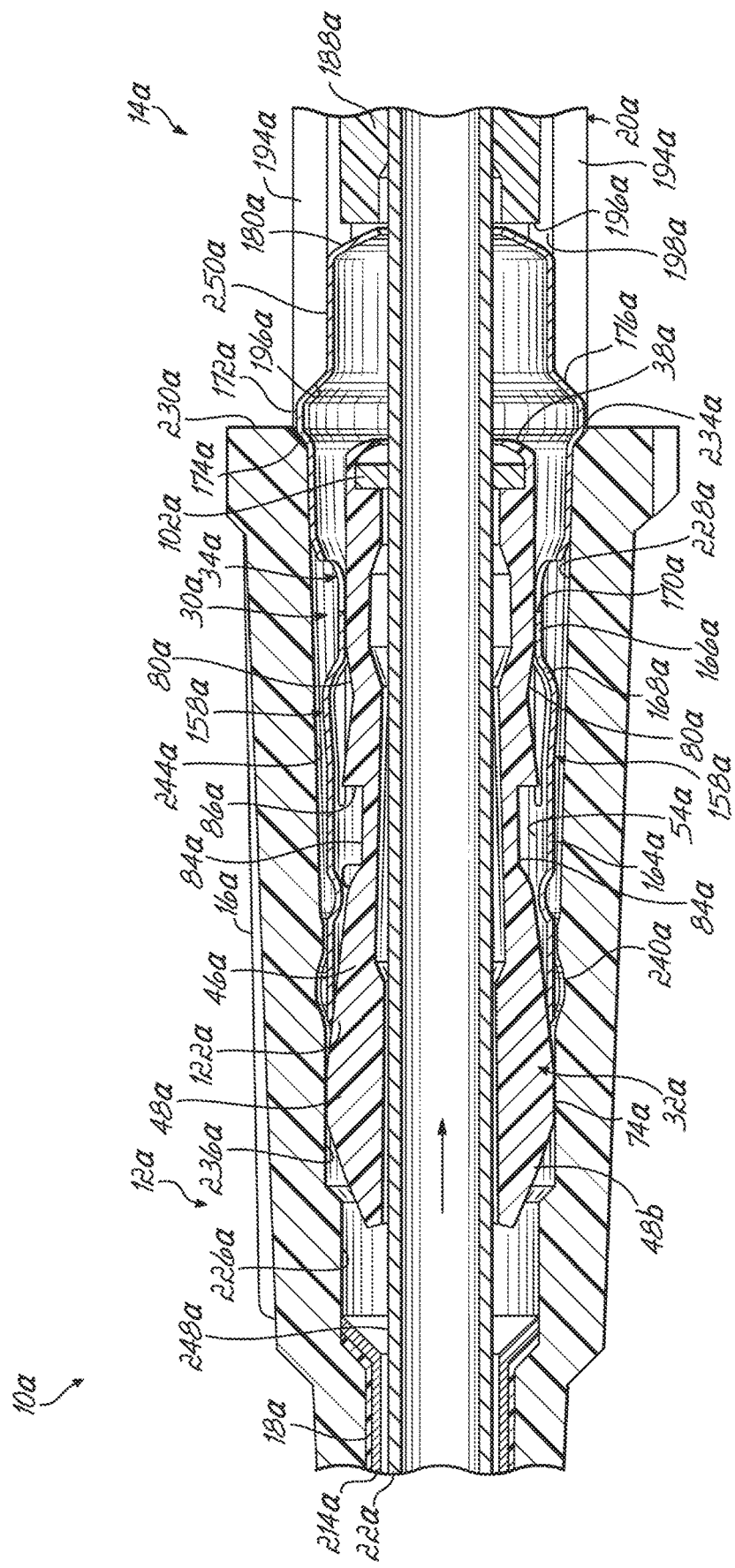
FIG. 22B is another partial cross-sectional view of the safety catheter of FIG. 22A in the ready position and 90.degree. offset from the view shown in FIG. 22A.

In addition to, or in lieu of, the projections 260 and corresponding notches 262 described above, various embodiments in accordance with the invention may include an inner member 32" having further features to restrict re-emergence of the needle cannula 22 by pushing the needle cannula 22 distally out of the tip protector 30. Again, such additional features may be desirable for the larger gauge (smaller cross dimensions) needle cannula 22. To this end, and as shown in FIG. 21, the inner surface 54 of at least one of the arms 48a, 48b may include one or more ribs 264 adjacent the distal end 40 of the arms 48a, 48b configured to further block the path of the needle cannula 22. For example, in one embodiment, the ribs 264 may completely close off the re-emergence path of the needle cannula 22 from the tip protector 30. The invention, however, is not limited to completely closing off the path. Similar to above, in an exemplary embodiment, ribs 264 may be formed in inner member 32" during, for example, molding thereof.

In one exemplary embodiment, one rib 264a may be located on one of the arms 48a, 48b and two adjacent ribs 264b, 264c may be located on the other of the arms 48a, 48b. When the arms 48a, 48b, close down in front of the distal needle tip 24, the ribs 264a-c may be configured to engage each other. For example, the one rib 264a may be configured to nest between the two adjacent ribs 264b, 264c when the inner member 32" is at least in the second position. In this way, should there be an attempt to move the needle cannula 22 distally relative to the tip protector 30 (either intentionally or accidentally), the tip 24 thereof would come into contact with the ribs 264 and be prevented from moving any further distally relative to the tip protector 30.

Those of ordinary skill in the art will recognize that the arrangement of ribs 264 is not limited to the particular arrangement shown and described herein, but encompasses a broad range of rib configurations designed to drop down in front of the distal needle tip 24 and block the re-emergence path of the needle cannula 22. It should also be recognized that the ribs 264 may be configured such that the ribs 264 do not engage the needle cannula 22 when in the ready position. In alternative embodiments, however, it should be recognized that the ribs 264 may engage and slide along the outer surface 248 of the needle cannula 22 during use.

Figure 23A:
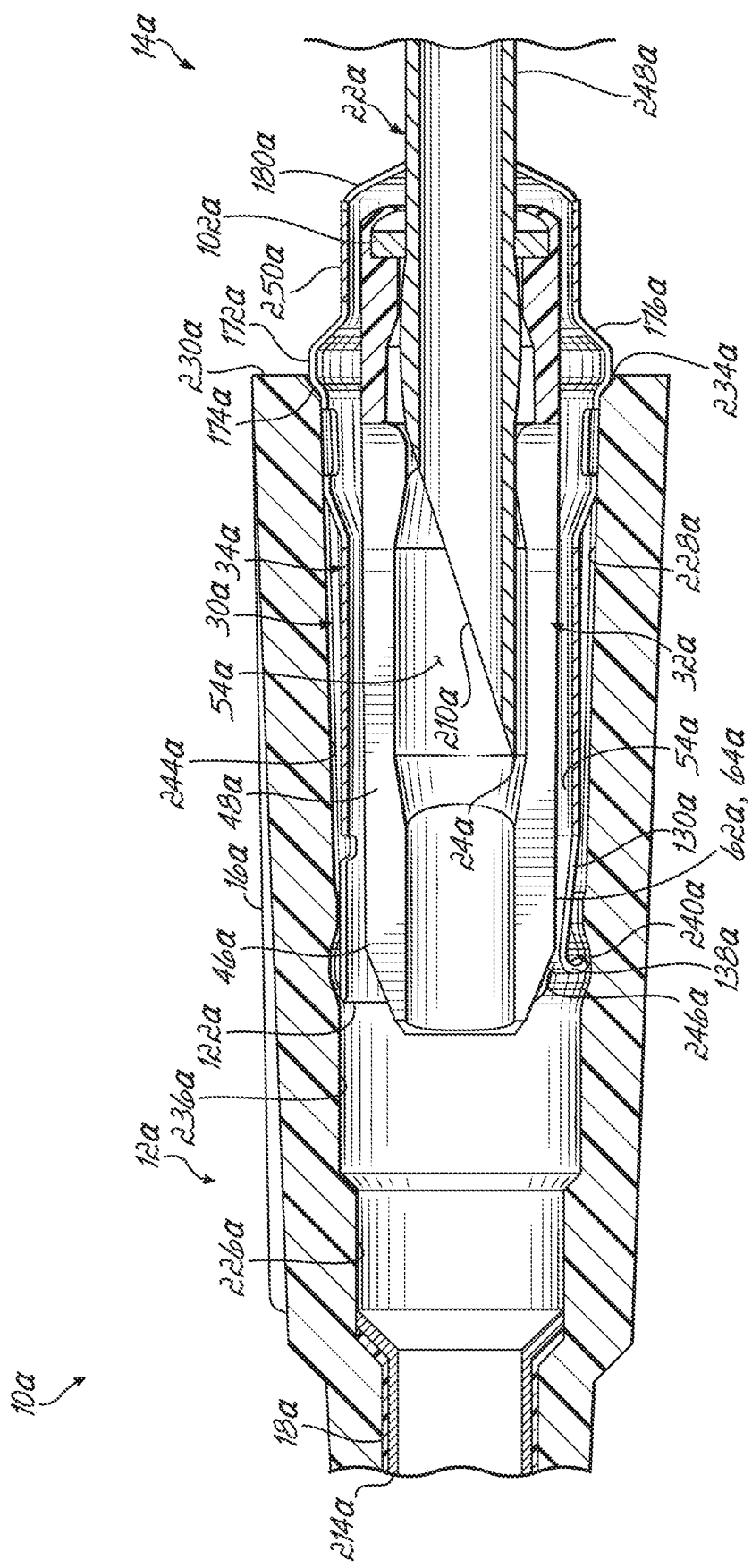
FIG. 23A is a partial cross-sectional view of the alternative safety catheter of FIG. 22A in the protected position, wherein the inner member is in a second position relative to the outer member.
Figure 23B:
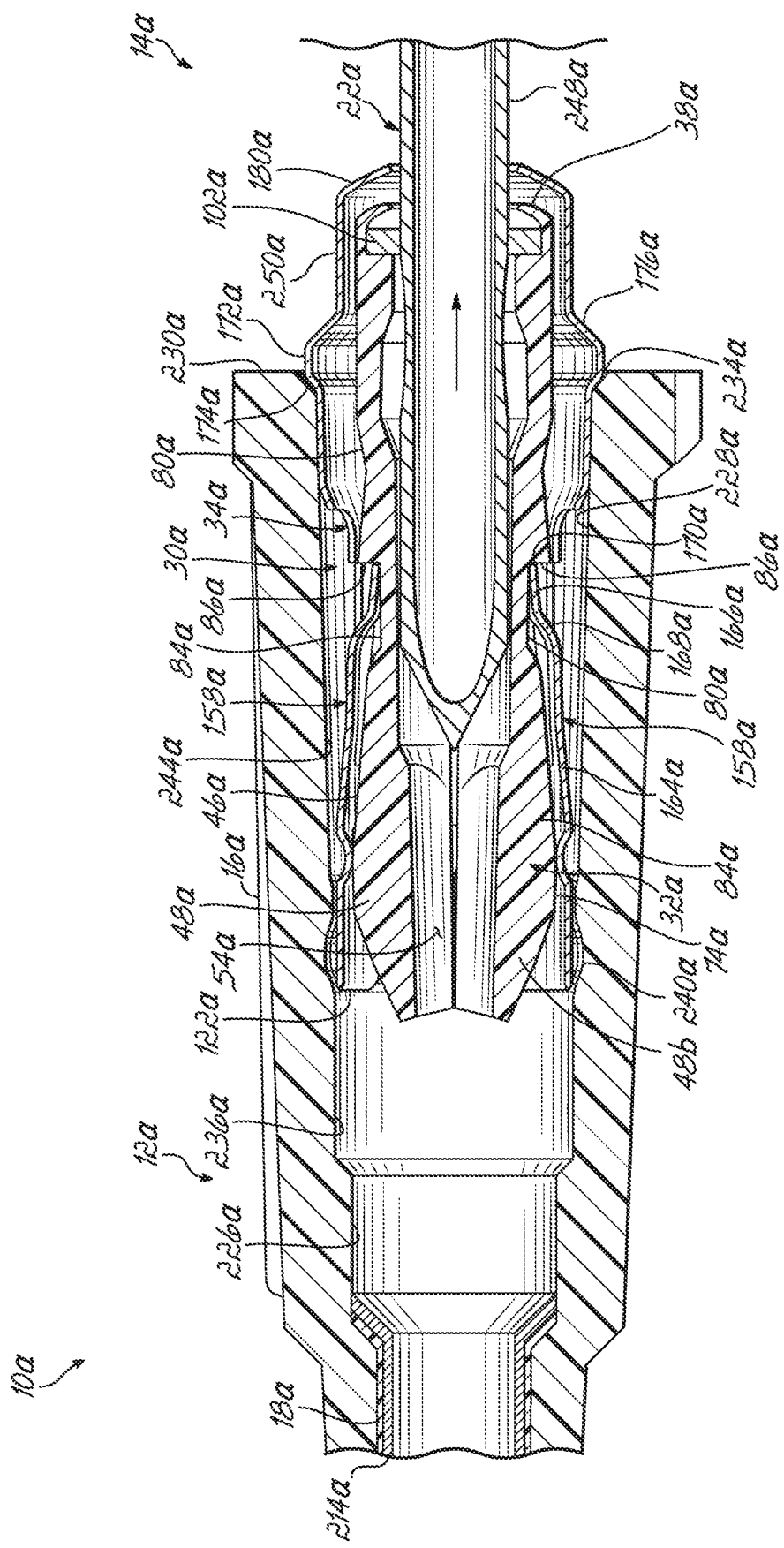
FIG. 23B is another partial cross-sectional view of the safety catheter of FIG. 23A in the protected position and 90.degree. offset from the view shown in FIG. 23A.

In the various embodiments described above, the inner member 32 remained within the outer member 34 in both the first position (e.g., the ready state of the safety catheter 10) and the second position (e.g., the protected state of the safety catheter 10). While this may provide certain advantages to enhancing the strength of the tip protector 30 or enhancing the shielding of the distal tip 24 of the needle cannula 22, the invention is not so limited. In this regard, FIGS. 22A-23B in which like reference numbers refer to like features in FIGS. 1-19, but succeeded by the letter a, illustrate an embodiment wherein the tip protector 30a includes an inner m ember 32a that projects out of the outer member 34a when in the first position. In this embodiment, the outer member 34a may be shorter in length as compared to outer member 34, for example, truncating near the distal end of flexible tabs 130a, such that the inner member 32a projects distally of the outer member 34a in the ready position. Tip protector 30a operates on similar principles as that described above. More particularly, those of ordinary skill in the art will appreciate that the interaction between the needle cannula 22a and the inner member 32a (e.g., stop washer 102a), the interaction between the inner member 32a and the outer member 34a, and the interaction between outer member 34a and catheter hub 16a remains substantially similar. FIGS. 23A and 23B show the tip protector 30a when in the protected position. In this position, the inner member 32a is substantially within the outer member 34a and the tip protector 30a is sufficiently secured to the needle cannula 22a to shield the distal tip 24a thereof.

Figure 24:
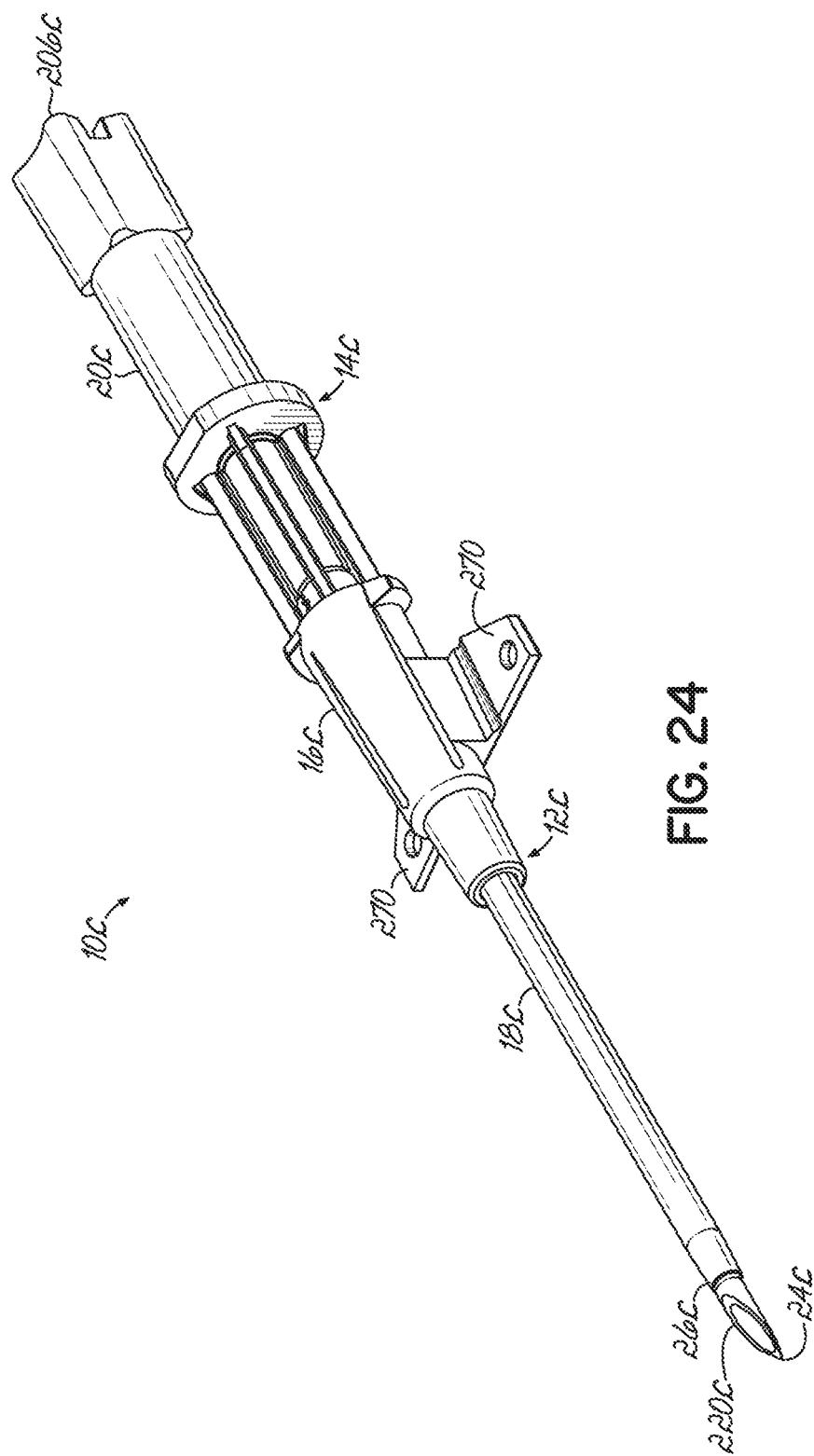
FIG. 24 is a perspective view of a safety catheter in accordance with another embodiment of the invention.

FIG. 24 in which like reference numbers refer to like features in FIGS. 1-19, but succeeded by the letter c illustrates a further alternative embodiment of a safety catheter 10c that is similar to the safety catheter 10 and includes a tip protector according to various embodiment as previously described above. As will be noted from the figure, the catheter assembly 12c includes a pair of wings 270 coupled to the catheter hub 16c on one side thereof in a conventional manner (e.g., patient side). As is generally known in the art, the wings 270 may be used to secure the catheter assembly 12c to the patient after being inserted therein using tape, for example.

Figure 25:
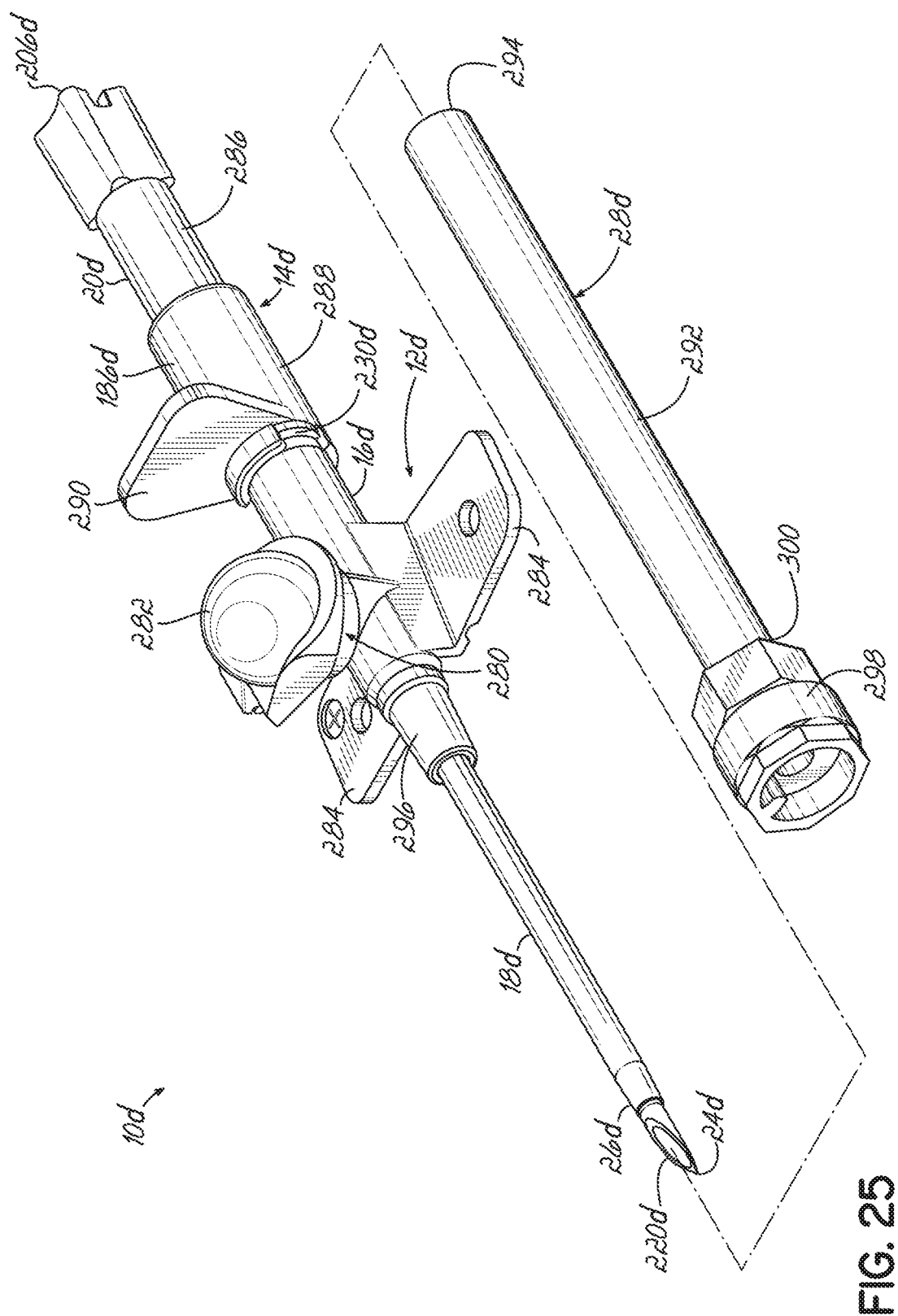
FIG. 25 is a perspective view of a safety catheter in accordance with yet another embodiment of the invention.

As illustrated by FIG. 25, the tip protector as described above may also be incorporated in a side port catheter design. In this regard, FIG. 25 in which like reference numbers refer to like features in FIGS. 1-19, but succeeded by the letter d, includes a safety catheter 10d that is similar to the safety catheter 10. The catheter assembly 12d includes a side port 280 formed therewith having a cover 282 selectively removable from the side port 280 for gaining access to the interior chamber 204d of the catheter hub 16d. As the construction and operation of a side port catheter is generally well understood in the art, a more complete description thereof will be omitted herein. As further shown in FIG. 25, in addition to the side port 280, the catheter assembly may also include a pair of wings 284 coupled to the catheter hub 16d. As shown, the needle hub 20d of catheter assembly 10d may have a slightly different design. In this regard, the body member 186d of the needle hub 20d may have a proximal portion 286 and a distal portion 288 being sized larger than the proximal portion 286 and configured so as to fit over the proximal end 230d of the catheter hub 16d. The needle hub 20d may also include a generally radially projecting tab 290 that facilitates use of the safety catheter 10d during, for example, insertion of the catheter assembly 12d into the vasculature of a patient.

The sheath 28d used with catheter insertion device 10d may also differ from sheath 28 described above. In this regard, the sheath 28d may include a straw-like tubular member 292 configured to shield the catheter tube 18d and needle cannula 22d during transit or storage of the catheter insertion device 10d. The proximal end 294 of the tubular member 292 may be configured to secure to the distal end 296 of the needle hub 20d through, for example, a friction fit. As illustrated in FIG. 25, the sheath 28d may include a plug 298 coupled to a distal end 300 of the tubular member 292. In use, the sheath 28d is removed from the catheter device 28d and the catheter assembly 12d is inserted into the patient as described above. After insertion, the plug 298 of sheath 28d may be secured to the proximal end 230d of the catheter hub 16d. The plug 298 effectively closes off the proximal end 230d of the catheter hub 16d such that communication between an external device and the vasculature of the patient is via the side port 280, as is generally understood in the art. Of course, instead of the plug 298 on sheath 28d being used in this capacity, other conventional methods may be used to close off the proximal end 230d of catheter hub 16d. In that case, the plug 298 on sheath 28d may be omitted.

While the present invention has been illustrated by the description of embodiments thereof, and while the embodiments have been described in considerable detail, it is not intended to restrict or in any way limit the scope of the appended claims to such detail. Additional advantages and modifications will readily appear to those skilled in the art.

For example, as discussed above, the interaction between the needle cannula and the inner member to cause movement of the inner member within the outer member includes the protuberance on needle cannula and the stop washer captured within the inner member. Other arrangements, however, are possible. For example, instead of having an outwardly projecting feature (e.g., protuberance 222) on the needle cannula, an inwardly projecting feature, such as an inwardly projecting cavity or groove may also be used (not shown). In this embodiment, the stop member associated with the inner member may be configured to drop into the cavity or groove to provide a positive lock between the inner member and the needle cannula. Similar to the above, the inner and outer members may be effectively locked together when the inner member is in the second position to limit relative movement therebetween. Thus, a flexible tab/cavity arrangement may be used to limit distal movement of the inner member relative to the outer member. Additionally, an opening in the proximal end of the outer member may be sized to restrict the passing of the inner member therethrough. It should be realized that because there is a positive lock between the inner member and the needle cannula in such an embodiment, the inner member may no longer need to block the path of the needle cannula when in the second position.

In addition to the above, depending on the specific application, the inner and outer members may be structurally enhanced so as to accommodate the stresses and strains imposed thereon during use. Accordingly, various ribbing, ridges, etc., may be selectively used to add strength in desired areas. By way of example, the outer member may include a containment ring (not shown) on its outer surface to increase the hoop strength of the outer member. The containment ring may be a separate element which is coupled to the outer member or be integrally formed, via material buildup in the desired area, with the outer member. In one embodiment, for example, a containment ring may be disposed adjacent the proximal end of slots, but configured not to interfere with the operation of the flexible tabs or indentations.

Thus, the invention in its broader aspects is, therefore, not limited to the specific details, representative apparatus and method, and illustrative examples shown and described. Accordingly, departures may be made from such details without departing from the spirit or scope of the general inventive concept.

The invention claimed is:

1. A needle tip protector adapted to be used with a safety catheter having a catheter hub having an inner wall, comprising:

a needle hub having a distal portion including a nose and a needle having a distal tip extending from the nose, an extension portion of the needle hub extending distally beyond the nose;

an outer member extending along an axial axis having a body including a proximal end and a distal end and at least one abutment surface adapted to be in contact with a counterpart surface of the catheter hub, the proximal end and at least a proximal portion of the body of the outer member surrounded by the extension portion of the needle hub when the needle tip protector is in a ready to use position;

an inner member positioned within the axial extent of the outer member and axially shiftable relative to the outer member within the axial extent of the outer member, the inner member having a distal end;

wherein the needle extends along the axial axis through the inner member with the distal tip extending beyond the distal end of the inner member when the needle tip protector is in the ready to use position;

a locking portion at the outer member in engagement with a bias portion at the inner member to provide a resistance force to movement of the inner member relative to the outer member during the initial movement of the needle as the needle is being withdrawn in a proximal direction;

wherein the inner member has two inward biasing opposing arms that are prevented from biasing inwardly by being in contact with the needle during the initial movement of the needle so as to maintain the locking portion and the bias portion in resistance engagement with each other to prevent relative axial movement between the inner member and the outer member and to bias the at least one abutment surface into contact with the counterpart surface to prevent relative movement between the outer member and the catheter hub;

wherein when the distal tip of the needle is withdrawn past the two inward biasing opposing arms, the two inward biasing opposing arms bias inwardly to the axial axis so as to no longer maintain the locking portion and the bias portion in resistance engagement with each other to allow axial movement of the inner member relative to the outer member; and wherein the two inward biasing opposing arms prevent the distal tip of the needle from re-emerging from the distal end of the inner member.

2. The needle tip protector of claim 1, wherein when the needle is further withdrawn along the proximal direction so that the inner member is further shifted axially along the proximal direction relative to the outer member, the locking portion and the bias portion act to prevent axial shifting of the inner member in a distal direction.

3. The needle tip protector of claim 1, further comprising a stop member associated with the inner member configured to cooperate with the needle during the withdrawal of the needle from the catheter hub of the safety catheter.

4. The needle tip protector of claim 3, wherein the stop member forms a proximal end face of the inner member against which a deformed feature proximate to the distal tip of the needle engages when the needle is withdrawn proximally relative to the outer member, the proximal end face of the inner member engages the proximal end of the body of the outer member when the inner member is fully withdrawn proximally relative to the outer member so that the inner and outer members may be withdrawn together and the needle tip protector may be removed from the catheter hub.

5. The needle tip protector of claim 1, wherein the needle has a deformed feature proximate to the distal tip that engages a stop member associated with the inner member so that the inner member is caused to be axially shifted proximally relative to the outer member when the needle is moved axially in the proximal direction.

6. The needle tip protector of claim 1, wherein the two inward biasing opposing arms bias generally inward relative to the axial axis, at least one the two inward biasing opposing arms having a projection to restrict the re-emergence of the needle from the inner member in a distal direction.

7. The needle tip protector of claim 1, wherein the needle tip protector is adapted to be used with the safety catheter, the safety catheter having a sideport catheter hub.

8. The needle tip of claim 1, wherein the body of the outer member includes a portion that projects generally outwardly from the body to engage with a proximal end of the catheter hub when the safety catheter is in the ready to use position.

9. The needle tip protector of claim 1, wherein the outer member has at least two abutment surfaces correspondingly provided by at least two flexible tabs and wherein the distal end of the inner member is defined by respective distal ends of the two inward biasing opposing arms, the at least two flexible tabs each being biased by a corresponding one of the two inward biasing opposing arms to maintain biased contact with the counterpart surface until the respective distal ends of the two inward biasing opposing arms are moved proximally relative to the outer member past the at least two flexible tabs.

10. A needle tip protector adapted to be used with a safety catheter that includes a catheter hub having a cavity defined by an inner surface, comprising:

an outer member extending along an axial axis having a body including a proximal end and a distal end and at least one abutment surface adapted to be in contact with a counterpart surface of the catheter hub;

an inner member positioned within the axial extent of the outer member and axially shiftable relative to the outer member within the axial extent of the outer member having two inward biasing opposing arms extending to a distal end positioned within the outer member and axially shiftable within the outer member;

a needle having a distal tip extending from a needle hub having an extension portion that surrounds at least a proximal portion including a proximal end of the outer member when the needle tip protector is in a ready to use position, the needle extending along the axial axis through the inner member with the distal tip extending beyond the distal end of the inner member so that the two inward biasing opposing arms are biased by the needle away from the axial axis when the needle tip protector is in the ready to use position, the at least one abutment surface configured to be in contact with the counterpart surface of the catheter hub to fixedly hold the outer member to the catheter hub when the two inward biasing opposing arms are biased by the needle away from the axial axis;

wherein when the distal tip of the needle is withdrawn proximally past the two inward biasing opposing arms, the two inward biasing opposing arms move inwardly toward the axial axis to prevent the distal tip of the needle from re-emerging from the distal end of the inner member and the outer member is no longer fixedly held to the catheter hub.

11. The needle tip protector of claim 10, further comprising a locking portion at the outer member in engagement with a bias portion at the inner member to provide a resistance force to movement of the inner member relative to the outer member during the initial movement of the needle as the needle is being withdrawn in a proximal direction.

12. The needle tip protector of claim 10, wherein the outer member has at least two abutment surfaces correspondingly provided by at least two flexible tabs and wherein the two inward biasing opposing arms have respective distal ends, the at least two flexible tabs each being biased by a corresponding one of the two inward biasing opposing arms to maintain biased contact with the counterpart surface until the respective distal ends of the two inward biasing opposing arms are moved proximally relative to the outer member past the at least two flexible tabs.

\* \* \* \* \*